(12) United States Patent
Kutsko et al.

(10) Patent No.: US 8,454,708 B2
(45) Date of Patent: *Jun. 4, 2013

(54) ARTICULABLE ANCHOR

(75) Inventors: James Kutsko, Carnation, WA (US);
Seung Yi, Aliso Viejo, CA (US); Clinton Lee Finger, Bellevue, WA (US)

(73) Assignee: Spiration, Inc., Redmond, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/754,394

(22) Filed: Apr. 5, 2010

(65) Prior Publication Data

US 2010/0262071 A1 Oct. 14, 2010

Related U.S. Application Data

(63) Continuation of application No. 11/585,415, filed on Oct. 24, 2006, now Pat. No. 7,691,151.

(60) Provisional application No. 60/787,995, filed on Mar. 31, 2006.

(51) Int. Cl.
*A61F 2/06* (2006.01)
*A61M 15/00* (2006.01)

(52) U.S. Cl.
USPC .................. 623/23.65; 623/9; 128/200.24

(58) Field of Classification Search
USPC .................. 623/9, 23.64–23.65; 604/892.1
See application file for complete search history.

(56) References Cited

U.S. PATENT DOCUMENTS 2,832,078 A 4/1958 Williams
2,981,254 A 4/1961 Vanderbilt (Continued)

FOREIGN PATENT DOCUMENTS

AU 2002239759 5/2002
CA 2308186 5/1999

(Continued)

OTHER PUBLICATIONS

U.S. Appl. No. 09/686,204, filed Oct. 10, 2000, and its ongoing prosecution history including without limitation Office Actions, Amendments, Remarks, and any other potentially relevant documents.

(Continued)

*Primary Examiner* — Suzette J Gherbi
(74) *Attorney, Agent, or Firm* — Knobbe, Martens, Olson & Bear, LLP

(57) ABSTRACT

An implantable device for providing one-way flow of air through a lumen in a human lung to reduce the volume of air trapped in a diseased portion of the lung by occluding the lumen to prevent inhalation while permitting expiration out of the diseased portion. The implantable device is deployable in the lumen with a catheter. The device comprises an umbrella-shaped, one-way valve. The valve is collapsible for containment within a catheter and expandable in situ when deployed to occlude the lumen. The valve defines a longitudinal axis and comprises a plurality of metal struts, a resilient membrane, and a central post. The device further comprises an anchor for securing the implantable device within the lumen. The anchor comprises a tapered distal end for penetrating the wall of the lumen, and a planar member positioned to limit advancement of the anchor into the lumen. The implantable device further comprises a mechanism connecting the one-way valve to the anchor. The mechanism is disposed along the longitudinal axis when the device is collapsed. The mechanism is configured to permit the valve to be oriented at an angle to said anchor when deployed. Accordingly, the anchor can be positioned in a section of the lumen that is at an angle to a section of said lumen in which said one-way valve is positioned.

20 Claims, 11 Drawing Sheets

U.S. PATENT DOCUMENTS

| | | |
|---|---|---|
| 3,320,972 A | 5/1967 | High et al. |
| 3,370,305 A | 2/1968 | Goott et al. |
| 3,445,916 A | 5/1969 | Schulte |
| 3,472,230 A | 10/1969 | Forgarty |
| 3,540,431 A | 11/1970 | Modin-Uddin |
| 3,617,060 A | 11/1971 | Iezzi |
| 3,657,744 A | 4/1972 | Ersek |
| 3,671,979 A | 6/1972 | Moulopoulos |
| 3,683,913 A | 8/1972 | Kurtz et al. |
| 3,757,783 A | 9/1973 | Alley |
| 3,760,808 A | 9/1973 | Bleuer |
| 3,788,327 A | 1/1974 | Donowitz et al. |
| 3,874,388 A | 4/1975 | King et al. |
| 4,014,318 A | 3/1977 | Dockum et al. |
| 4,040,428 A | 8/1977 | Clifford |
| 4,056,854 A | 11/1977 | Boretos et al. |
| 4,084,268 A | 4/1978 | Ionescu et al. |
| 4,086,665 A | 5/1978 | Poirier |
| 4,212,463 A | 7/1980 | Repinski et al. |
| 4,218,782 A | 8/1980 | Rygg |
| 4,222,126 A | 9/1980 | Boretos et al. |
| 4,250,873 A | 2/1981 | Bonnet |
| 4,301,810 A | 11/1981 | Belman |
| 4,302,854 A | 12/1981 | Runge |
| 4,339,831 A | 7/1982 | Johnson |
| RE31,040 E | 9/1982 | Possis |
| 4,403,616 A | 9/1983 | King |
| 4,456,016 A | 6/1984 | Nowacki et al. |
| 4,512,338 A | 4/1985 | Balko et al. |
| 4,533,137 A | 8/1985 | Sonne |
| 4,569,674 A | 2/1986 | Phillips et al. |
| 4,582,058 A | 4/1986 | Depel et al. |
| 4,592,741 A | 6/1986 | Vincent |
| 4,601,465 A | 7/1986 | Roy |
| 4,610,256 A | 9/1986 | Wallace |
| 4,619,246 A | 10/1986 | Molgaard-Nielsen et al. |
| 4,654,027 A | 3/1987 | Dragan et al. |
| 4,654,029 A | 3/1987 | D'Antonio |
| 4,681,110 A | 7/1987 | Wiktor |
| 4,684,363 A | 8/1987 | Ari et al. |
| 4,685,908 A | 8/1987 | Kurtz |
| 4,710,192 A | 12/1987 | Liotta et al. |
| 4,727,873 A | 3/1988 | Mobin-Uddin |
| 4,732,152 A | 3/1988 | Wallsten et al. |
| 4,745,925 A | 5/1988 | Dietz |
| 4,759,758 A | 7/1988 | Gabbay |
| 4,795,449 A | 1/1989 | Schneider et al. |
| 4,808,183 A | 2/1989 | Panje |
| 4,819,664 A | 4/1989 | Nazari |
| 4,822,354 A | 4/1989 | Elosegui |
| 4,830,003 A | 5/1989 | Wolff et al. |
| 4,832,680 A | 5/1989 | Haber et al. |
| 4,846,836 A | 7/1989 | Reich |
| 4,850,999 A | 7/1989 | Planck |
| 4,852,568 A | 8/1989 | Kensey |
| 4,877,025 A | 10/1989 | Hanson |
| 4,908,028 A | 3/1990 | Colon et al. |
| 4,934,999 A | 6/1990 | Bader |
| 4,936,823 A | 6/1990 | Colvin et al. |
| 4,968,294 A | 11/1990 | Salama |
| 4,973,047 A | 11/1990 | Norell |
| 4,979,505 A | 12/1990 | Cox |
| 4,984,581 A | 1/1991 | Stice |
| 5,033,312 A | 7/1991 | Stupecky |
| 5,038,621 A | 8/1991 | Stupecky |
| 5,059,208 A | 10/1991 | Coe et al. |
| 5,061,274 A | 10/1991 | Kensey |
| 5,078,739 A | 1/1992 | Martin |
| 5,092,781 A | 3/1992 | Casciotti et al. |
| 5,116,360 A | 5/1992 | Pinchuk et al. |
| 5,116,564 A | 5/1992 | Jansen et al. |
| 5,123,919 A | 6/1992 | Sauter et al. |
| 5,135,488 A | 8/1992 | Foote et al. |
| 5,151,105 A | 9/1992 | Kwan-Gett |
| 5,158,548 A | 10/1992 | Lau et al. |
| 5,161,524 A | 11/1992 | Evans |
| 5,171,299 A | 12/1992 | Heitzmann et al. |
| 5,197,980 A | 3/1993 | Gorshkov et al. |
| 5,255,687 A | 10/1993 | McKenna |
| 5,275,169 A | 1/1994 | Afromowitz et al. |
| 5,283,063 A | 2/1994 | Freeman |
| 5,300,050 A | 4/1994 | Everett, Jr. et al. |
| 5,304,199 A | 4/1994 | Myers |
| 5,306,234 A | 4/1994 | Johnson |
| 5,314,473 A | 5/1994 | Godin |
| 5,339,805 A | 8/1994 | Parker |
| 5,342,298 A | 8/1994 | Michaels et al. |
| 5,352,240 A | 10/1994 | Ross |
| 5,353,470 A | 10/1994 | Bartlett |
| 5,358,518 A | 10/1994 | Camilli |
| 5,366,478 A | 11/1994 | Brinkerhoff et al. |
| 5,370,657 A | 12/1994 | Irie |
| 5,382,261 A | 1/1995 | Palmaz |
| 5,383,470 A | 1/1995 | Kolbly |
| 5,391,205 A | 2/1995 | Knight |
| 5,392,775 A | 2/1995 | Adkins, Jr. et al. |
| 5,398,844 A | 3/1995 | Zaslavsky |
| 5,409,019 A | 4/1995 | Wilk |
| 5,409,444 A | 4/1995 | Kensey et al. |
| 5,411,507 A | 5/1995 | Heckele |
| 5,411,552 A | 5/1995 | Andersen et al. |
| 5,413,599 A | 5/1995 | Imachi et al. |
| 5,415,660 A | 5/1995 | Campbell et al. |
| 5,417,226 A | 5/1995 | Juma |
| 5,421,325 A | 6/1995 | Cinberg et al. |
| 5,445,626 A | 8/1995 | Gigante |
| 5,453,090 A | 9/1995 | Martinez et al. |
| 5,459,544 A | 10/1995 | Emura |
| 5,484,444 A | 1/1996 | Braunschweiler et al. |
| 5,486,154 A | 1/1996 | Kelleher |
| 5,499,995 A | 3/1996 | Teirstein |
| 5,500,014 A | 3/1996 | Quijano et al. |
| RE35,225 E | 4/1996 | Herweck et al. |
| 5,507,754 A | 4/1996 | Green et al. |
| 5,507,797 A | 4/1996 | Suzuki |
| 5,509,900 A | 4/1996 | Kirkman |
| 5,514,153 A | 5/1996 | Bonutti et al. |
| 5,549,626 A | 8/1996 | Miller et al. |
| 5,549,628 A | 8/1996 | Cooper et al. |
| 5,562,608 A | 10/1996 | Sekins et al. |
| 5,562,641 A | 10/1996 | Flomenblit et al. |
| 5,562,728 A | 10/1996 | Lazarus et al. |
| 5,603,698 A | 2/1997 | Roberts et al. |
| 5,607,469 A | 3/1997 | Frey |
| 5,645,565 A | 7/1997 | Rudd et al. |
| 5,647,857 A | 7/1997 | Anderson et al. |
| 5,660,175 A | 8/1997 | Dayal |
| 5,662,622 A | 9/1997 | Gore et al. |
| 5,662,713 A | 9/1997 | Andersen et al. |
| 5,669,933 A | 9/1997 | Simon et al. |
| 5,676,671 A | 10/1997 | Inoue |
| 5,683,451 A | 11/1997 | Lenker et al. |
| 5,690,644 A | 11/1997 | Yurek et al. |
| 5,693,089 A | 12/1997 | Inoue |
| 5,697,968 A | 12/1997 | Rogers et al. |
| 5,702,343 A | 12/1997 | Alferness |
| 5,702,409 A | 12/1997 | Rayburn et al. |
| 5,725,519 A | 3/1998 | Penner et al. |
| 5,752,522 A | 5/1998 | Murphy |
| 5,752,965 A | 5/1998 | Francis et al. |
| 5,755,770 A | 5/1998 | Ravenscroft |
| 5,763,979 A | 6/1998 | Mukherjee et al. |
| 5,782,896 A | 7/1998 | Chen et al. |
| 5,797,920 A | 8/1998 | Kim |
| 5,797,960 A | 8/1998 | Stevens et al. |
| 5,800,339 A | 9/1998 | Salama |
| 5,803,078 A | 9/1998 | Brauner |
| 5,810,837 A | 9/1998 | Hofmann et al. |
| 5,817,101 A | 10/1998 | Fiedler |
| 2,479,805 A | 11/1998 | Sabaratnam |
| 5,830,217 A | 11/1998 | Ryan |
| 5,833,694 A | 11/1998 | Poncet |
| 5,840,081 A | 11/1998 | Andersen et al. |
| 5,851,232 A | 12/1998 | Lois |
| 5,855,587 A | 1/1999 | Hyon |
| 5,855,597 A | 1/1999 | Jayaraman |
| 5,855,601 A | 1/1999 | Bessler et al. |

| | | | | | | |
|---|---|---|---|---|---|---|
| 5,876,434 | A | 3/1999 | Flomenblit et al. | 6,402,754 | B1 | 6/2002 | Gonzalez |
| 5,876,445 | A | 3/1999 | Andersen et al. | 6,416,554 | B1 | 7/2002 | Alferness et al. |
| 5,911,756 | A | 6/1999 | Debry | 6,425,916 | B1 | 7/2002 | Garrison et al. |
| 5,925,063 | A | 7/1999 | Khosravi | 6,428,561 | B1 | 8/2002 | Johansson-Ruden et al. |
| 5,944,738 | A | 8/1999 | Amplatz et al. | 6,439,233 | B1 | 8/2002 | Geertsema |
| 5,947,997 | A | 9/1999 | Pavcnik et al. | 6,440,164 | B1 | 8/2002 | DiMatteo et al. |
| 5,954,636 | A | 9/1999 | Schwartz et al. | 6,447,530 | B1 | 9/2002 | Ostrovsky et al. |
| 5,954,766 | A | 9/1999 | Zadno-Azizi et al. | 6,454,754 | B1 | 9/2002 | Frank |
| 5,957,949 | A | 9/1999 | Leonhardt et al. | 6,458,076 | B1 | 10/2002 | Pruitt |
| 5,957,978 | A | 9/1999 | Blom | 6,458,153 | B1 | 10/2002 | Bailey et al. |
| 5,972,009 | A | 10/1999 | Fortier et al. | 6,471,718 | B1 | 10/2002 | Staehle et al. |
| 5,976,158 | A | 11/1999 | Adams et al. | 6,471,979 | B2 | 10/2002 | New et al. |
| 5,976,174 | A | 11/1999 | Ruiz | 6,485,407 | B2 | 11/2002 | Alferness et al. |
| 5,984,965 | A | 11/1999 | Knapp et al. | 6,488,673 | B1 | 12/2002 | Laufer et al. |
| 5,989,234 | A | 11/1999 | Valerio et al. | 6,491,706 | B1 | 12/2002 | Alferness et al. |
| 6,003,517 | A | 12/1999 | Sheffield et al. | 6,493,589 | B1 | 12/2002 | Medhkour et al. |
| 6,007,575 | A | 12/1999 | Samuels | 6,503,272 | B2 | 1/2003 | Duerig et al. |
| 6,009,614 | A | 1/2000 | Morales | 6,510,846 | B1 | 1/2003 | O'Rourke |
| 6,010,511 | A | 1/2000 | Murphy | 6,514,290 | B1 | 2/2003 | Loomas |
| 6,010,525 | A | 1/2000 | Bonutti et al. | 6,527,761 | B1 | 3/2003 | Soltesz et al. |
| 6,020,380 | A | 2/2000 | Killian | 6,540,782 | B1 | 4/2003 | Snyders |
| 6,027,525 | A | 2/2000 | Suh et al. | 6,544,192 | B2 | 4/2003 | Starr et al. |
| 6,045,560 | A | 4/2000 | McKean et al. | 6,544,291 | B2 | 4/2003 | Taylor |
| 6,051,022 | A | 4/2000 | Cai et al. | 6,551,303 | B1 * | 4/2003 | Van Tassel et al. ........... 604/508 |
| 6,068,635 | A | 5/2000 | Gianotti | 6,558,429 | B2 | 5/2003 | Taylor |
| 6,068,638 | A | 5/2000 | Makower | 6,568,387 | B2 | 5/2003 | Davenport et al. |
| 6,077,291 | A | 6/2000 | Das | 6,569,166 | B2 | 5/2003 | Gonzalez |
| 6,079,413 | A | 6/2000 | Baran | 6,585,639 | B1 | 7/2003 | Kotmel et al. |
| 6,083,141 | A | 7/2000 | Hougen | 6,589,256 | B2 | 7/2003 | Forber |
| 6,083,255 | A | 7/2000 | Laufer et al. | 6,592,594 | B2 | 7/2003 | Rimbaugh et al. |
| 6,096,027 | A | 8/2000 | Layne | 6,599,311 | B1 | 7/2003 | Biggs et al. |
| 6,099,551 | A | 8/2000 | Gabbay | 6,600,307 | B2 | 7/2003 | Turski |
| 6,123,663 | A | 9/2000 | Rebuffat | 6,610,043 | B1 | 8/2003 | Ingenito |
| 6,132,458 | A | 10/2000 | Staehle et al. | 6,629,951 | B2 | 10/2003 | Laufer et al. |
| 6,135,729 | A | 10/2000 | Aber | 6,632,243 | B1 | 10/2003 | Zadno-Azizi et al. |
| 6,135,991 | A | 10/2000 | Muni et al. | 6,634,363 | B1 | 10/2003 | Danek et al. |
| 6,141,855 | A | 11/2000 | Morales | 6,638,285 | B2 | 10/2003 | Gabbay |
| 6,146,357 | A | 11/2000 | Addis | 6,669,724 | B2 | 12/2003 | Park et al. |
| 6,149,664 | A | 11/2000 | Kurz | 6,673,070 | B2 | 1/2004 | Edwards et al. |
| 6,162,245 | A | 12/2000 | Jayaraman | 6,679,264 | B1 | 1/2004 | Deem et al. |
| 6,165,179 | A | 12/2000 | Cathcart et al. | 6,682,250 | B2 | 1/2004 | Banks |
| 6,168,614 | B1 | 1/2001 | Andersen et al. | 6,682,520 | B2 | 1/2004 | Ingenito |
| 6,168,617 | B1 | 1/2001 | Blaeser et al. | 6,694,979 | B2 | 2/2004 | Deem et al. |
| 6,174,307 | B1 | 1/2001 | Daniel et al. | 6,709,401 | B2 | 3/2004 | Perkins et al. |
| 6,174,323 | B1 | 1/2001 | Biggs | 6,712,812 | B2 | 3/2004 | Roschak et al. |
| 6,183,520 | B1 | 2/2001 | Pintauro et al. | 6,716,208 | B2 | 4/2004 | Humes |
| 6,193,748 | B1 | 2/2001 | Thompson et al. | 6,722,360 | B2 | 4/2004 | Doshi |
| 6,200,333 | B1 | 3/2001 | Laufer | 6,743,259 | B2 | 6/2004 | Ginn |
| 6,203,551 | B1 | 3/2001 | Wu | 6,746,686 | B2 | 6/2004 | Hughes et al. |
| 6,206,918 | B1 | 3/2001 | Campbell et al. | 6,749,606 | B2 | 6/2004 | Keast et al. |
| 6,210,338 | B1 | 4/2001 | Afremov et al. | 6,749,658 | B1 | 6/2004 | Seagren |
| 6,231,587 | B1 | 5/2001 | Makower | 6,840,952 | B2 | 1/2005 | Saker et al. |
| 6,231,589 | B1 | 5/2001 | Wessman et al. | 6,849,049 | B2 | 2/2005 | Starr et al. |
| 6,234,996 | B1 | 5/2001 | Bagaoisan et al. | 6,849,084 | B2 | 2/2005 | Rabkin et al. |
| 6,238,334 | B1 | 5/2001 | Easterbrook, III et al. | 6,860,847 | B2 | 3/2005 | Alferness et al. |
| 6,240,615 | B1 | 6/2001 | Kimes et al. | 6,887,256 | B2 | 5/2005 | Gilson |
| 6,241,654 | B1 | 6/2001 | Alferness | 6,904,909 | B2 | 6/2005 | Andreas et al. |
| 6,241,678 | B1 | 6/2001 | Afremov et al. | 6,911,028 | B2 | 6/2005 | Shadduck |
| 6,241,758 | B1 | 6/2001 | Cox | 6,929,637 | B2 | 8/2005 | Gonzalez et al. |
| 6,242,472 | B1 | 6/2001 | Sekins et al. | 6,941,950 | B2 | 9/2005 | Wilson et al. |
| 6,245,102 | B1 | 6/2001 | Jayaraman | 6,951,571 | B1 | 10/2005 | Srivastava |
| 6,258,100 | B1 | 7/2001 | Alferness et al. | 6,955,675 | B2 | 10/2005 | Jain |
| 6,264,700 | B1 | 7/2001 | Kilcoyne et al. | 6,958,076 | B2 | 10/2005 | Acosta et al. |
| 6,267,775 | B1 | 7/2001 | Clerc et al. | 6,989,027 | B2 | 1/2006 | Allen et al. |
| 6,270,527 | B1 | 8/2001 | Campbell et al. | 6,997,951 | B2 | 2/2006 | Solem et al. |
| 6,287,290 | B1 | 9/2001 | Perkins et al. | 7,011,094 | B2 | 3/2006 | Rapacki et al. |
| 6,287,334 | B1 | 9/2001 | Moll et al. | 7,100,616 | B2 | 9/2006 | Springmeyer |
| 6,293,951 | B1 | 9/2001 | Alferness et al. | 7,141,046 | B2 | 11/2006 | Perkins et al. |
| 6,299,604 | B1 | 10/2001 | Ragheb et al. | 7,169,140 | B1 | 1/2007 | Kume |
| 6,302,893 | B1 | 10/2001 | Limon et al. | 7,175,644 | B2 | 2/2007 | Cooper et al. |
| 6,312,407 | B1 | 11/2001 | Zadno-Azizi et al. | 7,207,946 | B2 | 4/2007 | Sirokman |
| 6,325,777 | B1 | 12/2001 | Zadno-Azizi et al. | 7,252,086 | B2 | 8/2007 | Tanaka |
| 6,325,778 | B1 | 12/2001 | Zadno-Azizi et al. | 7,278,430 | B2 | 10/2007 | Kumar |
| 6,327,772 | B1 | 12/2001 | Zadno-Azizi et al. | 7,357,795 | B2 | 4/2008 | Kaji et al. |
| 6,328,689 | B1 | 12/2001 | Gonzalez et al. | 7,412,977 | B2 | 8/2008 | Fields et al. |
| 6,338,728 | B1 | 1/2002 | Valerio et al. | 7,434,578 | B2 * | 10/2008 | Dillard et al. ........... 128/200.24 |
| 6,350,278 | B1 | 2/2002 | Lenker et al. | 7,476,203 | B2 | 1/2009 | DeVore et al. |
| 6,355,014 | B1 | 3/2002 | Zadno-Azizi et al. | 7,530,995 | B2 | 5/2009 | Quijano et al. |
| 6,398,775 | B1 | 6/2002 | Perkins et al. | 7,533,671 | B2 | 5/2009 | Gonzalez et al. |

| | | | |
|---|---|---|---|
| 7,691,151 B2 | 4/2010 | Kutsko | |
| 7,704,268 B2 * | 4/2010 | Chanduszko | 606/213 |
| 7,757,692 B2 | 7/2010 | Alferness et al. | |
| 7,798,974 B2 | 9/2010 | Sirokman | |
| 7,842,010 B2 | 11/2010 | Bonnette et al. | |
| 7,842,061 B2 * | 11/2010 | Dillard et al. | 606/191 |
| 7,854,228 B2 | 12/2010 | Wilson et al. | |
| 7,862,500 B2 * | 1/2011 | Khairkhahan et al. | 600/16 |
| 7,875,048 B2 | 1/2011 | Dillard et al. | |
| 7,887,585 B2 | 2/2011 | Gonzalez et al. | |
| 7,896,887 B2 | 3/2011 | Rimbaugh et al. | |
| 7,942,931 B2 * | 5/2011 | Gonzalez et al. | 623/9 |
| 8,177,809 B2 * | 5/2012 | Mavani et al. | 606/213 |
| 8,192,478 B2 * | 6/2012 | Khairkhahan et al. | 623/1.11 |
| 8,257,381 B2 * | 9/2012 | Dillard et al. | 606/191 |
| 2001/0010017 A1 | 7/2001 | Letac et al. | |
| 2002/0077564 A1 | 6/2002 | Campbell et al. | |
| 2002/0077593 A1 | 6/2002 | Perkins et al. | |
| 2002/0077696 A1 | 6/2002 | Zadno-Azizi et al. | |
| 2002/0095209 A1 | 7/2002 | Zadno-Azizi et al. | |
| 2002/0112729 A1 | 8/2002 | DeVore et al. | |
| 2002/0123749 A1 | 9/2002 | Jain | |
| 2002/0147462 A1 | 10/2002 | Mair et al. | |
| 2003/0018327 A1 | 1/2003 | Truckai et al. | |
| 2003/0050648 A1 | 3/2003 | Alferness et al. | |
| 2003/0051733 A1 | 3/2003 | Kotmel et al. | |
| 2003/0055331 A1 | 3/2003 | Kotmel et al. | |
| 2003/0109869 A1 | 6/2003 | Shadduck | |
| 2003/0125763 A1 | 7/2003 | McInnes | |
| 2003/0127090 A1 | 7/2003 | Gifford et al. | |
| 2003/0154988 A1 | 8/2003 | DeVore | |
| 2003/0181922 A1 | 9/2003 | Alferness | |
| 2003/0183235 A1 | 10/2003 | Rimbaugh et al. | |
| 2003/0195385 A1 | 10/2003 | DeVore | |
| 2003/0212412 A1 | 11/2003 | Dillard et al. | |
| 2003/0216769 A1 | 11/2003 | Dillard et al. | |
| 2003/0225445 A1 | 12/2003 | Derus et al. | |
| 2004/0010209 A1 | 1/2004 | Sirokman | |
| 2004/0039250 A1 | 2/2004 | Tholfsen et al. | |
| 2004/0059263 A1 | 3/2004 | DeVore | |
| 2004/0194780 A1 | 10/2004 | Doshi | |
| 2004/0200484 A1 | 10/2004 | Springmeyer | |
| 2004/0206349 A1 | 10/2004 | Alferness et al. | |
| 2004/0210224 A1 | 10/2004 | Ahmad et al. | |
| 2004/0210248 A1 | 10/2004 | Gordon et al. | |
| 2004/0211412 A1 | 10/2004 | Alferness et al. | |
| 2004/0243140 A1 | 12/2004 | Alferness et al. | |
| 2005/0033310 A1 | 2/2005 | Alferness et al. | |
| 2005/0033344 A1 | 2/2005 | Dillard et al. | |
| 2005/0096721 A1 | 5/2005 | Mangin et al. | |
| 2005/0137611 A1 | 6/2005 | Escudero et al. | |
| 2005/0137714 A1 | 6/2005 | Gonzalez et al. | |
| 2005/0145253 A1 | 7/2005 | Wilson et al. | |
| 2005/0166925 A1 | 8/2005 | Wilson et al. | |
| 2005/0222580 A1 | 10/2005 | Gifford, III et al. | |
| 2005/0267323 A1 | 12/2005 | Dorros et al. | |
| 2006/0032497 A1 | 2/2006 | Doshi | |
| 2006/0074382 A1 | 4/2006 | Gonzalez et al. | |
| 2006/0155217 A1 | 7/2006 | DeVore | |
| 2006/0200076 A1 | 9/2006 | Gonzalez et al. | |
| 2006/0206147 A1 | 9/2006 | DeVore et al. | |
| 2006/0235432 A1 | 10/2006 | DeVore | |
| 2006/0235467 A1 | 10/2006 | DeVore | |
| 2006/0241745 A1 * | 10/2006 | Solem | 623/2.18 |
| 2006/0249164 A1 | 11/2006 | Springmeyer | |
| 2006/0270940 A1 | 11/2006 | Tsukashima et al. | |
| 2007/0185531 A1 | 8/2007 | Rimbaugh et al. | |
| 2007/0221230 A1 | 9/2007 | Thompson et al. | |
| 2007/0225747 A1 | 9/2007 | Perkins et al. | |
| 2007/0232992 A1 | 10/2007 | Kutsko et al. | |
| 2007/0250022 A1 | 10/2007 | Sirokman | |
| 2008/0015627 A1 | 1/2008 | DeVore | |
| 2008/0119866 A1 | 5/2008 | Alferness | |
| 2008/0132989 A1 | 6/2008 | Snow et al. | |
| 2009/0099530 A1 | 4/2009 | Adams et al. | |
| 2009/0182369 A1 * | 7/2009 | Gonzalez et al. | 606/191 |
| 2009/0205667 A1 | 8/2009 | Alferness et al. | |
| 2009/0292262 A1 | 11/2009 | Adams et al. | |
| 2010/0256714 A1 | 10/2010 | Springmeyer | |
| 2011/0054632 A1 * | 3/2011 | Alferness et al. | 623/23.65 |
| 2012/0289989 A1 * | 11/2012 | Dillard et al. | 606/191 |

FOREIGN PATENT DOCUMENTS

| | | |
|---|---|---|
| CA | 2375752 | 1/2001 |
| CA | 2401331 | 3/2001 |
| CA | 2408923 | 11/2001 |
| CN | 101868199 | 10/2010 |
| DE | 100 04 979 | 8/2000 |
| EP | 0 665 029 | 8/1995 |
| EP | 0 743 071 | 11/1996 |
| EP | 1 151 729 | 11/2001 |
| EP | 1 157 663 | 11/2001 |
| EP | 1 206 276 | 5/2002 |
| EP | 1 198 269 | 10/2009 |
| EP | 03 716 212 | 12/2010 |
| GB | 2 082 071 | 3/1982 |
| GB | 2 324 729 | 11/1998 |
| GB | 2 348 138 | 9/2000 |
| JP | 58-163332 | 9/1983 |
| JP | 60-10740 | 1/1994 |
| JP | 2003-503162 | 1/2003 |
| JP | 2003-512129 | 4/2003 |
| JP | 2004-535887 | 12/2004 |
| JP | 2005-527297 | 9/2005 |
| JP | 3742010 | 11/2005 |
| JP | 2008-513141 | 5/2008 |
| JP | 4387803 B2 | 10/2009 |
| JP | 2011-500171 | 1/2011 |
| RU | 2140211 | 10/1999 |
| SU | 852321 | 8/1981 |
| SU | 1371700 | 2/1988 |
| SU | 1593651 | 9/1990 |
| WO | WO 88/09683 | 12/1988 |
| WO | WO 94/26175 | 11/1994 |
| WO | WO 95/32018 | 11/1995 |
| WO | WO 96/34582 | 11/1996 |
| WO | WO 96/37167 | 11/1996 |
| WO | WO 97/09932 | 3/1997 |
| WO | WO 97/13471 | 4/1997 |
| WO | WO 97/27893 | 8/1997 |
| WO | WO 97/42871 | 11/1997 |
| WO | WO 97/44085 | 11/1997 |
| WO | WO 98/00840 | 1/1998 |
| WO | WO 98/01084 | 1/1998 |
| WO | WO 98/19633 | 5/1998 |
| WO | WO 98/39047 | 9/1998 |
| WO | WO 98/44854 | 10/1998 |
| WO | WO 98/48706 | 11/1998 |
| WO | WO 99/01076 | 1/1999 |
| WO | WO 99/13801 | 3/1999 |
| WO | WO 99/26692 | 6/1999 |
| WO | WO 99/32040 | 7/1999 |
| WO | WO 99/42059 | 8/1999 |
| WO | WO 99/42161 | 8/1999 |
| WO | WO 99/59503 | 11/1999 |
| WO | WO 99/64109 | 12/1999 |
| WO | WO 00/18329 | 4/2000 |
| WO | WO 00/27292 A | 5/2000 |
| WO | WO 00/42950 | 7/2000 |
| WO | WO 00/51500 A | 9/2000 |
| WO | WO 00/51510 | 9/2000 |
| WO | WO 00/62699 | 10/2000 |
| WO | WO 00/78386 | 12/2000 |
| WO | WO 00/78407 | 12/2000 |
| WO | WO 01/02042 | 1/2001 |
| WO | WO 01/03641 | 1/2001 |
| WO | WO 01/03642 | 1/2001 |
| WO | WO 01/05334 | 1/2001 |
| WO | WO 01/10313 | 2/2001 |
| WO | WO 01/10314 | 2/2001 |
| WO | WO 01/12104 | 2/2001 |
| WO | WO 01/13839 | 3/2001 |
| WO | WO 01/13908 | 3/2001 |
| WO | WO 01/28433 | 4/2001 |
| WO | WO 01/30266 A | 5/2001 |
| WO | WO 01/37897 | 5/2001 |
| WO | WO 01/45590 | 6/2001 |

| | | |
|---|---|---|
| WO | WO 01/49213 | 7/2001 |
| WO | WO 01/52775 | 7/2001 |
| WO | WO 01/54585 | 8/2001 |
| WO | WO 01/54625 | 8/2001 |
| WO | WO 01/54685 | 8/2001 |
| WO | WO01/66190 | 9/2001 |
| WO | WO 01/66190 | 9/2001 |
| WO | WO 01/70114 | 9/2001 |
| WO | WO 01/74271 | 10/2001 |
| WO | WO 01/87170 | 11/2001 |
| WO | WO 01/89366 | 11/2001 |
| WO | WO 01/95786 | 12/2001 |
| WO | WO 02/05884 | 1/2002 |
| WO | WO 02/22072 | 3/2002 |
| WO | WO 02/32333 | 4/2002 |
| WO | WO 02/34322 | 5/2002 |
| WO | WO 02/38038 | 5/2002 |
| WO | WO 02/47575 | 6/2002 |
| WO | WO 02/056794 | 7/2002 |
| WO | WO 02/064045 | 8/2002 |
| WO | WO 02/064190 | 8/2002 |
| WO | WO 02/069823 | 9/2002 |
| WO | WO 02/094087 | 11/2002 |
| WO | WO 03/022124 | 3/2003 |
| WO | WO 03/030975 | 4/2003 |
| WO | WO 03/003946 | 5/2003 |
| WO | WO 03/034927 | 5/2003 |
| WO | WO 03/041779 | 5/2003 |
| WO | WO 03/047468 | 6/2003 |
| WO | WO 03/078579 | 9/2003 |
| WO | WO 03/088820 | 10/2003 |
| WO | WO 03/094996 | 11/2003 |
| WO | WO 03/099164 | 12/2003 |
| WO | WO 2004/010845 | 5/2004 |
| WO | WO 2004/080347 | 9/2004 |
| WO | WO 2005/013835 | 2/2005 |
| WO | WO 2006034166 A2 | 3/2006 |
| WO | WO 2007/123690 | 11/2007 |
| WO | WO 2009/049261 | 4/2009 |
| WO | WO 2009/135070 | 11/2009 |
| WO | WO 2010/118056 | 10/2010 |

OTHER PUBLICATIONS

U.S. Appl. No. 09/379,972, filed Aug. 24, 1999, Pub. No. 2010/0256714, published Oct. 7, 2010 and its ongoing prosecution history including without limitation Office Actions, Amendments, Remarks, and any other potentially relevant documents.
U.S. Appl. No. 10/052,875, filed Oct. 25, 2001, Pub. No. 2003/0083671, published May 1, 2003, and its ongoing prosecution history including without limitation Office Actions, Amendments, Remarks, and any other potentially relevant documents.
U.S. Appl. No. 09/881,862, filed Jun. 14, 2001, Pub. No. 2001/0052344, published Dec. 20, 2001 and its ongoing prosecution history including without limitation Office Actions, Amendments, Remarks, and any other potentially relevant documents.
U.S. Appl. No. 10/091,712, filed Mar. 6, 2002, Pub. No. 2002/0112729, published Aug. 22, 2002, and its ongoing prosecution history including without limitation Office Actions, Amendments, Remarks, and any other potentially relevant documents.
U.S. Appl. No. 10/317,667, filed Dec. 11, 2002, Pub. No. 2003/0158515, published Aug. 21, 2003, and its ongoing prosecution history including without limitation Office Actions, Amendments, Remarks, and any other potentially relevant documents.
U.S. Appl. No. 10/409,785, filed Apr. 8, 2003, and its ongoing prosecution history including without limitation Office Actions, Amendments, Remarks, and any other potentially relevant documents.
U.S. Appl. No. 10/259,007, filed Sep. 26, 2002, Pub. No. 2003/0212337, published Nov. 13, 2003, and its ongoing prosecution history including without limitation Office Actions, Amendments, Remarks, and any other potentially relevant documents.
U.S. Appl. No. 10/744,577, filed Dec. 22, 2003, Pub. No. 2004/0167636, published Aug. 26, 2004, and its ongoing prosecution history including without limitation Office Actions, Amendments, Remarks, and any other potentially relevant documents.
U.S. Appl. No. 11/260,012, filed Oct. 26, 2005, Pub. No. 2006/0155217, published Jul. 13, 2006, and its ongoing prosecution history including without limitation Office Actions, Amendments, Remarks, and any other potentially relevant documents.
U.S. Appl. No. 10/745,401, filed Dec. 22, 2003, Pub. No. 2005/0137714, published Jun. 23, 2005, and its ongoing prosecution history including without limitation Office Actions, Amendments, Remarks, and any other potentially relevant documents.
U.S. Appl. No. 11/585,415, filed Oct. 24, 2006, Pub. No. 2007/0232992, published Oct. 4, 2007, and its ongoing prosecution history including without limitation Office Actions, Amendments, Remarks, and any other potentially relevant documents.
U.S. Appl. No. 12/428,287, filed Apr. 22, 2009, Pub. No. 2009/0205667, published Aug. 20, 2009, and its ongoing prosecution history including without limitation Office Actions, Amendments, Remarks, and any other potentially relevant documents.
U.S. Appl. No. 11/738,412, filed Apr. 20, 2007, Pub. No. 2007/0250022, published Oct. 25, 2007, and its ongoing prosecution history including without limitation Office Actions, Amendments, Remarks, and any other potentially relevant documents.
U.S. Appl. No. 10/746,981, filed Dec. 23, 2003, Pub. No. 2004/0143282, published Jul. 22, 2004, and its ongoing prosecution history including without limitation Office Actions, Amendments, Remarks, and any other potentially relevant documents.
U.S. Appl. No. 10/933,778, filed Sep. 3, 2004, Pub. No. 2005/0033344, published Feb. 10, 2005, and its ongoing prosecution history including without limitation Office Actions, Amendments, Remarks, and any other potentially relevant documents.
U.S. Appl. No. 12/398,122, filed Mar. 4, 2009, Pub. No. 2009/0182369, published Jul. 16, 2009, and its ongoing prosecution history including without limitation Office Actions, Amendments, Remarks, and any other potentially relevant documents.
U.S. Appl. No. 11/733,710, filed Apr. 10, 2007, Pub. No. 2007/0185531, published Aug. 9, 2007, and its ongoing prosecution history including limitation Office Actions, Amendments, Remarks, and any other potentially relevant documents.
U.S. Appl. No. 10/150,547, filed May 17, 2002, and its ongoing prosecution history including without limitation Office Actions, Amendments, Remarks, and any other potentially relevant documents.
U.S. Appl. No. 10/178,073, filed Jun. 21, 2001, and its ongoing prosecution history including without limitation Office Actions, Amendments, Remarks, and any other potentially relevant documents.
U.S. Appl. No. 09/951,105, filed Sep. 11, 2001, and its ongoing prosecution history including without limitation Office Actions, Amendments, Remarks, and any other potentially relevant documents.
U.S. Appl. No. 10/178,073, filed Jun. 21, 2002, and its ongoing prosecution history including wothout limitation Office Actions, Amendments, Remarks, and any other potentially relevant documents.
U.S. Appl. No. 10/103,487, filed Mar. 20, 2002, and its ongoing prosecution history including without limitation Office Actions, Amendments, Remarks, and any other potentially relevant documents.
U.S. Appl. No. 10/418,929, filed Apr. 17, 2003, and its ongoing prosecution history including without limitation Office Actions, Amendments, Remarks, and any other potentially relevant documents.
U.S. Appl. No. 10/124,790, filed Apr. 16, 2002, and its ongoing prosecution history including without limitation Office Actions, Amendments, Remarks, and any other potentially relevant documents.
U.S. Appl. No. 10/143,353, filed May 9, 2002, and its ongoing prosecution history including without limitation Office Actions, Amendments, Remarks, and any other potentially relevant documents.
U.S. Appl. No. 10/196,513, filed Jul. 15, 2002, and its ongoing prosecution history including without limitation Office Actions, Amendments, Remarks, and any other potentially relevant documents.

U.S. Appl. No. 10/254,392, filed Sep. 24, 2002, and its ongoing prosecution history including without limitation Office Actions, Amendments, Remarks, and any other potentially relevant documents.
U.S. Appl. No. 10/827,384, filed Apr. 19, 2004, and its ongoing prosecution history including without limitation Office Actions, Amendments, Remarks, and any other potentially relevant documents.
U.S. Appl. No. 10/847,554, filed May 17, 2004, and its ongoing prosecution history including without limitation Office Actions, Amendments, Remarks, and any other potentially relevant documents.
U.S. Appl. No. 10/387,963, filed Mar. 12, 2003, and its ongoing prosecution history including without limitation Office Actions, Amendments, Remarks, and any other potentially relevant documents.
U.S. Appl. No. 10/847,427, filed May 17, 2004, and its ongoing prosecution history including without limitation Office Actions, Amendments, Remarks, and any other potentially relevant documents.
U.S. Patent Application Serial No. 10/48,041, filed May 18, 2004, and its ongoing prosecution history including without limitation Office Actions, Amendments, Remarks, and any other potentially relevant documents.
U.S. Appl. No. 10/848,571, filed Feb. 10, 2005, and its ongoing prosecution history including without limitation Office Actions, Amendments, Remarks, and any other potentially relevant documents.
U.S. Appl. No. 11/178,640, filed Jul. 11, 2005, and its ongoing prosecution history including without limitation Office Actions, Amendments, Remarks, and any other potentially relevant documents.
U.S. Appl. No. 11/204,383, filed Aug. 15, 2005, and its ongoing prosecution history including without limitation Office Actions, Amendments, Remarks, and any other potentially relevant documents.
U.S. Appl. No. 11/417,738, May 3, 2006, and its ongoing prosecution history including without limitation Office Actions, Amendments, Remarks, and any other potentially relevant documents.
U.S. Appl. No. 11/418,541, filed May 3, 2006, and its ongoing prosecution history including without limitation Office Actions, Amendments, Remarks, and any other potentially relevant documents.
U.S. Appl. No. 11/417,553, filed May 3, 2006, and its ongoing prosecution history including without limitation Office Actions, Amendments, Remarks, and any other potentially relevant documents.
U.S. Appl. No. 11/416,337, filed May 2, 2006, and its ongoing prosecution history including without limitation Office Actions, Amendments, Remarks, and any other potentially relevant documents.
U.S. Appl. No. 11/417,944, filed May 3, 2006, and its ongoing prosecution history including without limitation Office Actions, Amendments, Remarks, and any other potentially relevant documents.
U.S. Appl. No. 11/781,130, filed Jul. 20, 2007, and its ongoing prosecution history including without limitation Office Actions, Amendments, Remarks, and any other potentially relevant documents.
U.S. Appl. No. 11/880,090, filed Jul. 19, 2007, and its ongoing prosecution history including without limitation Office Actions, Amendments, Remarks, and any other potentially relevant documents.
U.S. Appl. No. 12/249,243, filed Oct. 10, 2008, and its ongoing prosecution history including without limitation Office Actions, Amendments, Remarks, and any other potentially relevant documents.
U.S. Appl. No. 12/422,179, filed Apr. 10, 2009, and its ongoing prosecution history including without limitation Office Actions, Amendments, Remarks, and any other potentially relevant documents.
U.S. Appl. No. 12/721,426, filed Mar. 10, 2010, and its ongoing prosecution history including without limitation Office Actions, Amendments, Remarks, and any other potentially relevant documents.
U.S. Appl. No. 12/828,629, filed Jul. 1, 2010, and its ongoing prosecution history including without limitation Office Actions, Amendments, Remarks, and any other potentially relevant documents.
Amendment mailed Mar. 3, 2004 in response to Office Action dated Oct. 3, 2003 in the related copending U.S. Appl. No. 09/951,105.
Andre A. Kulisz, Autocath 100—Nonsurgical, Intraurethral Bladder Control Device for Urinary Incontinent and Urinary Retentive Women—Another Dr. Kulisz's Development, http://www.kulisz.com/autocath.htm, 2003, 3 pp.
Article: Autocath® 100—Nonsurgical, Intraurethral Bladder Control Device for Incontinent and Retentive Women—Dr. Kulisz's Development.
Chest Drains, from webmaster@atroi.ed/cp., from website Mar. 21, 2002; pp. 1-3.
Chest Drains, from webmaster@surgical-tutor.org.uk; from Website on Mar. 21, 2002; pp. 1-3.
Dillard et al.,"Evaluation of a Nvel Intra-bronchial Valve Device to Produce Lung Volume Reduction," Poster show at conference in Jun. 2002.
EDO Certamics Products and Services, from webmaster@edocorp.com; from website on Mar. 21, 2002; pp. 1,2.
Ellis, James H., Balloon Catheter Occlusion of Bronchopleural Fistulae, May 7, 1981, AJR: 138, Jan. 1982, p. 157-159.
EWS Endobronchial Watanabe Spigots, Novatech, edited Apr. 17, 2002.
Exploring Chest Drain Options; from webmaster google.com; RNWeb: Continuing Education; from website on Mar. 21, 2002; pp. 1-6.
Harris et al., "The Experimental Production in Dogs of Emphysema with Associated Asthatic Syndrome by Means of an Interatracheal Ball Valve," J Exp Med 30:1919; 75-88.
Horiuchi et al: Three Cases of Intractable Pneumothorax Treated Sucessfully by Bronchial Embolization using Silicon; JJSB, 2001. pp. 25-30.
Inaspettato: Endoscopic Treatment of Bronchopleural Fistulas Using N-butyl-2-cyanoacrylate; Surgical Laparoscopy & Endoscopy; vol. 4 No. 1, pp. 62-64, 1994.
Jones et al: Closure of a Benign Broncho-Oesophageal Fistula by Endoscopic Injection of Bovine Collagen, Cyanocrylate Glue and Gelfoam; 1996, pp. 53-55 Aust. N.Z. J.. Surg.
Lewis et al, "Pulmonary Interstitial Emphysema: Selective Bronchial Occlusion with a Swan-Ganz Catheter." Archives of Disease in Childhood, 63:1988, 313-315.
Marco: Bubble Detector, from webmaster@marco.de, from Website on Mar. 21, 2002; pp. 1-3.
Matthew et al. "Selective Bronchial Obstruction for Treatment of Bullous Interstitial Emphysema," J. of Ped. 96:1980, 475-477.
Oasis Dry Suction Chest Drains; Instructions for Use; Atrium Medical Corporation, Hudson New Hampshire, on Mar. 27, 2002,pp. 1-4.
Okada et al: Emergent Bronchofiberoptic Bronchial Occlusion for Intractable Pneumothorax with Severe Emphysema; The Japanese Journal of Thoracic and Cardiovascular Surgery, 1998. pp. 1078-1081.
Puhakka et al., "Acute Bronchial Obstruction: An Experimental Rabbit Model Study." Int. J. of Pediatric Otorhinolaryngology. 18:1989, 107-118.
SIII Control and Display Modules; from webmaster@stoeckert.de; from website on Mar. 21, 2002, pp. 15.
Snider et al., "The Definition of Emphysema: Report of the National Heart Lung and Blood Institute, Division of Lung Diseases Workshop", Am. Ev. Respir. Dis., 132:182-185, 1985.
Tube Thorascostomy; from webmaster@merck.com/pubs/mmanual; from Website Mar. 21, 2003, pp. 1,2.
Understanding Chest Drainage; from webmaster@nursingceu.com; from website on Mar. 21, 2002; pp. 1-15.
Watanabe et al: Bronchial Embolization Using Dental Impression Material in a Case of Pyelo-bronchial Fistula with *Candida fungemia*; 1991. Journal of the Japan Society for Bronchology, pp. 607-610.
PCT Search Report and Written Opinion from corresponding PCT Application No. PCT/US2004/007721, mailed Mar. 12, 2004, 14 pp.
International Search Report in International application No. PCT/US00/40701, mailed Jan. 25, 2001, 3 pp.

European Supplemental Search Report in European Appln. No. 00969008.2, dated Feb. 26, 2004, 5 pp.
US Office Action mailed Oct. 3, 2003 from related copending U.S. Appl. No. 09/951,105.
International Search Report in International application No. PCT/US02/25555, mailed Mar. 19, 2003, 4 pp.
European Search Report in European Appln. No. 02759335.9, dated Jan. 31, 2007.
Extended European Search Report for EP 08 0205468, dated Jul. 28, 2009.
Canadian Office Action dated Apr. 28, 2009 for Canadian Application No. 2,459,702.
Canadian Office Action dated Mar. 9, 2010 for Canadian Application No. 2,459,702.
Canadian Office Action dated Dec. 14, 2010 for Canadian Application No. 2,459,702.
European Supplemental Search Report dated Nov. 19, 2009 for EP Application No. 03 71 0804.
European Examination Report dated Apr. 14, 2010 for EP Application No. 03 71 0804.
International Search Report of Jul. 7, 2003, Application No. PCT/US03/05968.
European Supplemental Search Report of Feb. 28, 2008, Application No. 03 716 212.0-1265.
European Office Action of Dec. 23, 2008, Application No. 03 716 212.0-1265.
European Office Action of Dec. 8, 2010, Application No. 09739872.1.
Australian Office Action of Oct. 29, 2007, Application No. 2003219927.
Canadian Office Action of Apr. 28, 2009, Application No. 2,479,805.
Japanese Office Action of Feb. 3, 2009, Application No. 2003-577779.
US Office Action of Feb. 8, 2006, U.S. Appl. No. 10/103,487, filed Mar. 3, 2002.
US Office Action of Jun. 14, 2005, U.S. Appl. No. 10/103,487, filed Mar. 3, 2002.
US Office Action of Mar. 22, 2007, U.S. Appl. No. 10/103,487, filed Mar. 3, 2002.
US Office Action of May 19, 2006, U.S. Appl. No. 10/103,487, filed Mar. 3, 2002.
US Office Action of Oct. 20, 2004, U.S. Appl. No. 10/103,487, filed Mar. 3, 2002.
US Office Action of Sep. 12, 2006, U.S. Appl. No. 10/103,487, filed Mar. 3, 2002.
US Office Action of Dec. 10, 2010, U.S. Appl. No. 11/880,090, filed Jul. 19, 2007.
Canadian Office Action dated Nov. 5, 2009, re Application No. 2,484,086 in 2 pgs.
International Search Report dated Oct. 1, 2003 re PCT Application No. PCT/US2003/14868.
PCT International Search Report from corresponding PCT Application No. PCT/US2007/007923, dated May 20, 2008 in 2 pages, re.
PCT Preliminary and Written Report from corresponding PCT Application No. PCT/US2007/007923, dated Sep. 30, 2008 in 7 pages, re.
Chinese Office Action dated Jun. 4, 2010 re CN Application No. 200780019455.6.
International Preliminary Report on Patentability dated Dec. 23, 2009 re PCT/US2008/079650.
International Search Report dated Jan. 30, 2009 re PCT/US2008/079650.
International Search Report and Written Opinion for Application No. PCT/US2010/030131, dated Jun. 18, 2010.
International Search Report and Written Opinion for Application No. PCT/US2004/025458, mailed Nov. 30, 2004.
Russian Office Action, for App. No. 2008139081/14(050381), dated Nov. 24, 2010.
JP 2009-503031 Office Action dated Mar. 2, 2012 and English translation in 9 pages.
Notice of Reasons for Rejection in Japanese application No. 2009-503031 mailed on Jul. 10, 2012 in six pages.
English Translation of Chinese First Office Action for Chinese Application No. 201110022562.2, issued on Sep. 28, 2012 in 12 pages.

* cited by examiner

ARTICULABLE ANCHOR

RELATED APPLICATIONS

This application is a continuation of U.S. application Ser. No. 11/585,415, filed Oct. 24, 2006 now U.S. Pat. No. 7,691,151, which claims the benefit under 35 U.S.C. 119(c) to U.S. Provisional Patent Application No. 60/787,995, filed Mar. 31, 2006. The foregoing applications are hereby incorporated by reference in their entirety.

BACKGROUND OF THE INVENTION

1. Field of the Invention

The inventions relate in general to the field of pulmonary treatments, and specifically to systems, devices, and methods for treating a patient's lung or portion thereof.

2. Description of the Related Art

Chronic Obstructive Pulmonary Disease ("COPD") has become a major cause of morbidity and mortality in the United States. COPD is typically characterized by the presence of airflow obstructions due to chronic bronchitis or emphysema. The airflow obstructions in COPD are due largely to structural abnormalities in the smaller airways in the lungs.

Mortality, health-related costs, and the segment of the population having adverse effects due to COPD are substantial. COPD is a progressive disease that can severely affect a person's ability to accomplish normal tasks. One method of treating COPD is the insertion of one-way valves into lumens in the lung. The valves inhibit inhalation, but permit exhalation of air already within the lung. The lung presents challenge in mounting such valves because lumens within it are rarely linear over a useful distance. Accordingly, there is a need for a device to permit mounting of valves within non-linear lumens in the lung.

SUMMARY OF THE INVENTION

Accordingly, one aspect of the invention comprises an implantable device for providing substantially one-way flow of air through a lumen in a human lung to reduce the volume of air trapped in a diseased portion of the lung. The implantable device occludes the lumen to substantially prevent inhalation while substantially permitting expiration out of said diseased portion of the lung. The implantable device is deployable into the lumen with a catheter.

One aspect of an embodiment of the implantable device can comprise a one-way valve being generally umbrella-shaped in configuration. The valve is collapsible for containment within a delivery catheter and expandable in situ when deployed. The valve substantially occludes the lumen. The valve is configured so that when deployed in an orientation to substantially preclude inhalation, inhaled air is prevented from flowing past the valve into said lung by capturing said air within the umbrella-shaped valve. The air exerts an outward force on the umbrella shape and forces said valve to tightly engage the lumen. The valve is configured to permit expiration to occur between the perimeter of the valve and the lumen.

The valve also defines a longitudinal axis and comprises a plurality of metal struts that define a generally bell-shaped frame. Each of the struts have a first end that curves slightly inward towards the longitudinal axis of said implantable device when deployed and a second end proximal a junction of the second ends of the other struts. The valve also has a resilient membrane that wraps around at least a part of the metal struts and is supported by them. The membrane extends from the junction of the plurality of metal struts toward the first end of said struts. The valve also comprises a central post with a first part that extends within the membrane from the junction of said plurality of metal struts at the center of the bell-shaped frame. The post has a flange at an end distal from the strut junction. The flange is configured to permit deployment, positioning, and recapture of said implantable device. The central post further comprises a second part that extends axially outside the membrane.

Another aspect of the invention comprises an anchor for securing the implantable device within the lumen by inhibiting migration of the device once deployed. The anchor comprises a plurality of resilient arms extending outwardly and radially from the second part of the central post. Each of said arms are configured so as to be collapsible for containment within a delivery catheter and expandable to engage the lumen when deployed in situ. Each of the arms comprises a generally tapered distal end to permit the arm to penetrate the wall of the lumen. The arms further comprise a planar member proximal the tapered distal end and positioned at an angle to the arm to limit advancement of said arm into the lumen wall by contacting the surface of said lumen wall.

Another aspect of the invention comprises a mechanism connecting the one-way valve to the anchor and being disposed generally along the longitudinal axis when the device is in a collapsed state. The mechanism is configured to permit the valve to be oriented at an angle to the anchor when deployed, thereby allowing the anchor to be positioned in a section of the lumen that is at an angle to a section of said lumen in which the one-way valve is positioned. The mechanism comprises at least one connector at a first end to connect the mechanism to the valve. In some embodiments, the mechanism comprises a flexible member configured to be articulable to permit angled orientation of the anchor. In some embodiments, the flexible member comprises a helical spring. In some embodiments, the flexible member comprises a generally cylindrical mesh.

In some embodiments of the connector, a second end of the mechanism comprises a generally spherical connector. In some embodiments, the second end of the mechanism resides in a cavity within the anchor. In some embodiments the cavity is elongated. In some embodiments, the first end of the mechanism comprises a generally spherical connector.

In some embodiments, a cavity is within the anchor, wherein the first end of the mechanism can reside. In some embodiments, the implantable device comprises a second end of the mechanism which comprises a generally spherical connector. In some embodiments, the second end of the mechanism resides in a cavity within the valve. In some embodiments, at least one of the cavities is elongated.

Another aspect of an embodiment is an implantable device for deployment in an anatomical lumen wherein the device comprises an occluding device and an articulable anchor for securing the occluding device within the lumen in a manner that permits the anchor to articulate substantially with respect to said occluding device. The articulable anchor comprises a mechanism connecting said anchor to the occluding device. Additionally, the mechanism comprises at least one connector at a first end to connect said mechanism to at least one anchoring member and the articulable anchor includes a cavity.

DETAILED DESCRIPTION OF THE PREFERRED EMBODIMENT

Figure 1:
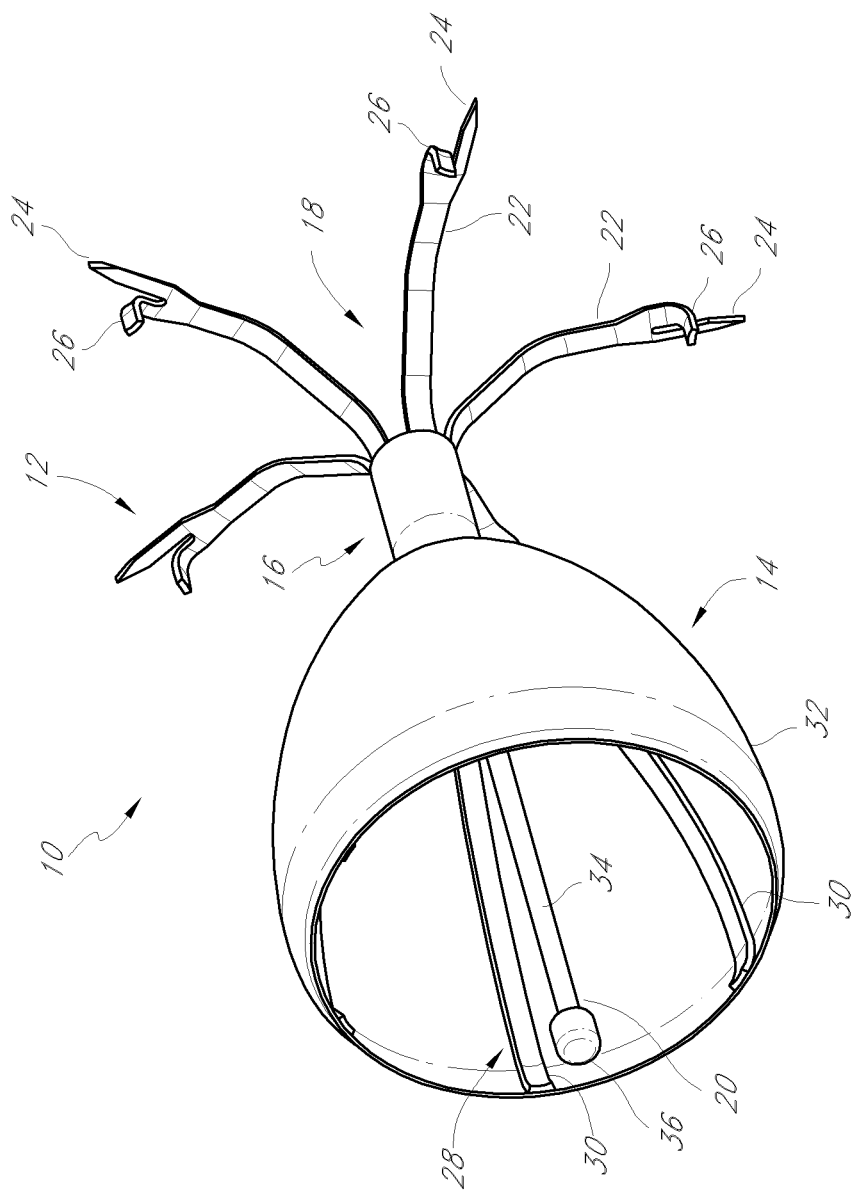
FIG. 1 is a perspective view of an implantable device with a one-way valve, an anchor, and a connector.

FIG. 1 illustrates an implantable device in an expanded position. The implantable device 10 is configured to affect airflow in an air passageway in a lung. The implantable device comprises an anchor 12 and an obstruction member 14. A connecting mechanism 16 couples the anchor 12 to the obstruction member 14. The illustrated implantable device 10 includes a support structure 18 that can form the frame of the implantable device 10. At least a portion of the anchor 12, the connecting mechanism 16, and the obstruction member 14 can be formed by the support structure 18. An elongated member 20 extends axially through obstruction member 14 and can be directly or indirectly coupled to the support structure 18.

The obstruction member 14 surrounds at least a portion of the elongated member 20 and is configured to interact with an anatomical lumen, such as an air passageway, to regulate the flow of fluid through the lumen. The obstruction member 14 can effectively function as a one-way valve. One example of an obstruction member is an occluding device.

The anchor 12 comprises a plurality of anchor members 22 that extend from the connecting mechanism 16. In the illustrated embodiment, each of the anchor members 22 is an elongated member that extends radially outward from the connecting mechanism 16 and terminates at a piercing end 24, although the anchor members 22 can have any number of piercing ends. One or more stops 26 can be positioned along each anchor member 22, preferably positioned at some point near the piercing members 24. The stops 26 can be configured to limit the puncturing by the piercing member 24 through lung tissue beyond a desired depth.

The stops 26 can be formed by splitting the distal ends of the anchor members 22. One of the split sections can be bent downwardly to form the stop 26, while leaving the second split section to extend outwardly to form the piercing member 24. Although the stops 26 can be formed integrally with the anchor member 22, the stops 26 can also be applied in a subsequent process. For example, each stop 26 can be a piece of metal that is mounted to the anchor members 22. Thus, each of the anchor members 22 can be of a one piece or multi-piece construction.

Any number of anchor members 22 can be used to limit migration of the implantable device 10 implanted at a desired deployment site. The illustrated implantable device 10 comprises five anchor members 22 that are coupled to the connecting mechanism 16. However, the anchor 12 can comprise any suitable number of anchor members in any various configurations. A skilled artisan can select the number of anchor members 22 based on the size of an air passageway, anchor design, and the like. The anchor members 22 can be positioned at regular or irregular intervals. When the anchor 12 is positioned in situ, the piercing members 24 can engage tissue of an air passageway wall of a lung to retain the implantable device 10 at a desired location. One non-limiting example of such an engagement occurs when at least one piercing member punctures the wall of the air passageway.

With continued reference to FIG. 1, the obstruction member 14 is generally umbrella-shaped and comprises an obstructing member frame 28 that carries a membrane 32. The obstructing frame 28 includes a plurality of arcuate struts 30 that support the membrane 32.

A plurality of pathways can be defined by the obstruction member 14 between each pair of struts 30. When the implantable device 10 is securely anchored in a lung passageway, the struts 30 can bias the obstruction member 14 outwardly against the air passageway wall. Between each pair of struts 30, the membrane 32 can define the pathway that permits mucus transport past the obstruction member 14 through the associated air passageway.

Proper mucociliary functioning can be maintained to ensure that the respiratory system continues to self clean after an implantable device has been deployed. To maintain mucociliary transport the membrane 32 can be folded inwardly away from the air passageway wall, especially during exhalation when the implantable device 10 has the anchor 12 positioned distally. The membrane 32 can press lightly against the air passageway wall in order to permit cilliary action for the movement of mucus past the membrane 32. Of course, the implantable device can have other configurations that permit mucus transport.

The membrane 32 can be treated to enhance sealing, improve biostability, and/or enhance mucus transport. To enhance valving action, the membrane 32 can be treated with a material that interacts with a wall of an air passageway to improve functioning. A coating on the membrane can reduce airflow in at least one direction between the air passageway and the expanded membrane engaging the air passageway wall. The coating can be a hydrogel that helps the membrane 32 adhere to the air passageway wall to further limit air flow past the implantable device in at least one direction. Other coating materials can be applied to the membrane or other portions of the implantable device depending on the intended application. The coating can be applied before, during, or after the implantable device is placed in a passageway.

In some embodiments, the membrane 32 can be coated with a lubricious material to limit adherence to an air passageway. Additionally, an implantable device may partially or fully collapse when subjected to rapid pressure changes, such as when a person coughs. If the membrane is folded together, the lubricious material can inhibit sticking of the membrane to itself so that the implantable device can quickly re-expand to function effectively again.

The implantable device can be adapted to facilitated movement through a delivery lumen. To reduce frictional forces between the implantable device and a lumen of a delivery instrument, a release agent can be applied to the implantable device. The release agent can reduce the force required to eject the implantable device out of the lumen as detailed above.

The struts can have first strut ends connected to the connecting mechanism 16 and opposing second strut ends. The proximal tips of the struts can curve radially inward toward the longitudinal axis of the implantable device 10.

With continued reference to FIG. 1, the elongated member 20 comprises a rod 34 that is connected to the connecting mechanism 16 and a gripping head 36. The rod 34 is a generally cylindrical body that extends along the longitudinal axis of the implantable device 10, although the rod 34 can be at other suitable locations. For example, the rod 34 can be angled or offset from the longitudinal axial of the implantable device 10.

The rod 34 is connected to the gripping head 36 that is positioned exterior to the chamber defined by the membrane 32. The rod 34 extends from the opening such that the gripping head 36 is spaced outwardly from the opening defined by the membrane 32. The elongated member 20 can be of such a length that it extends beyond the second end of the struts when the implantable 10 occupies an expanded position. When the gripping head 36 is spaced from the proximal ends of the struts and the membrane 32, a removal device (not shown) can easily grip the exposed gripping head 36. In alternative embodiments, the rod 34 terminates to form the gripping head 36 positioned inwardly of the opening defined by the member 32. Other embodiments of the gripping head 36 can include various changes in shape and size of the gripping head 36 to cooperate with different coupling mechanisms.

The elongated member 20 can also be of such a length that the elongated member 20 and the struts 30 extend substantially the same distance from the connecting mechanism 16 when the implantable device 10 is in a fully collapsed state (not shown). The struts 30 can lie flat along the rod 34 for a low profile configuration. The gripping head 36 preferably remains exposed so that the implantable device 10 can be pushed out of a delivery instrument by conveniently applying a force to the gripping head 36.

A variety of removal devices can be used to engage the implantable device to, for example, reposition, re-implant, or remove the implantable device as discussed above. The enlarged gripping head 36 can be designed to facilitate removal of the implantable device 10 by any of numerous extracting devices and methods as are known in the art. The removal gripping head 36 can be gripped by a removal device (such as forceps, an extractor, a retractor, gripping device, or other suitable device for gripping a portion of the implantable device 10). A sufficient proximal force can be applied to displace the implanted implantable device 10 from the implantation site. The illustrated gripping head 36 is a somewhat cylindrical knob having an outer diameter that is greater than the outer diameter of the rod 34. The gripping head 36 can have other configurations for engaging a removal device. Exemplary gripping heads can comprise a hook, ring, enlarged portion, connectors (e.g., snap connector, threaded connector, etc), or other structure for permanently or temporarily coupling to a removal device.

Figure 2:
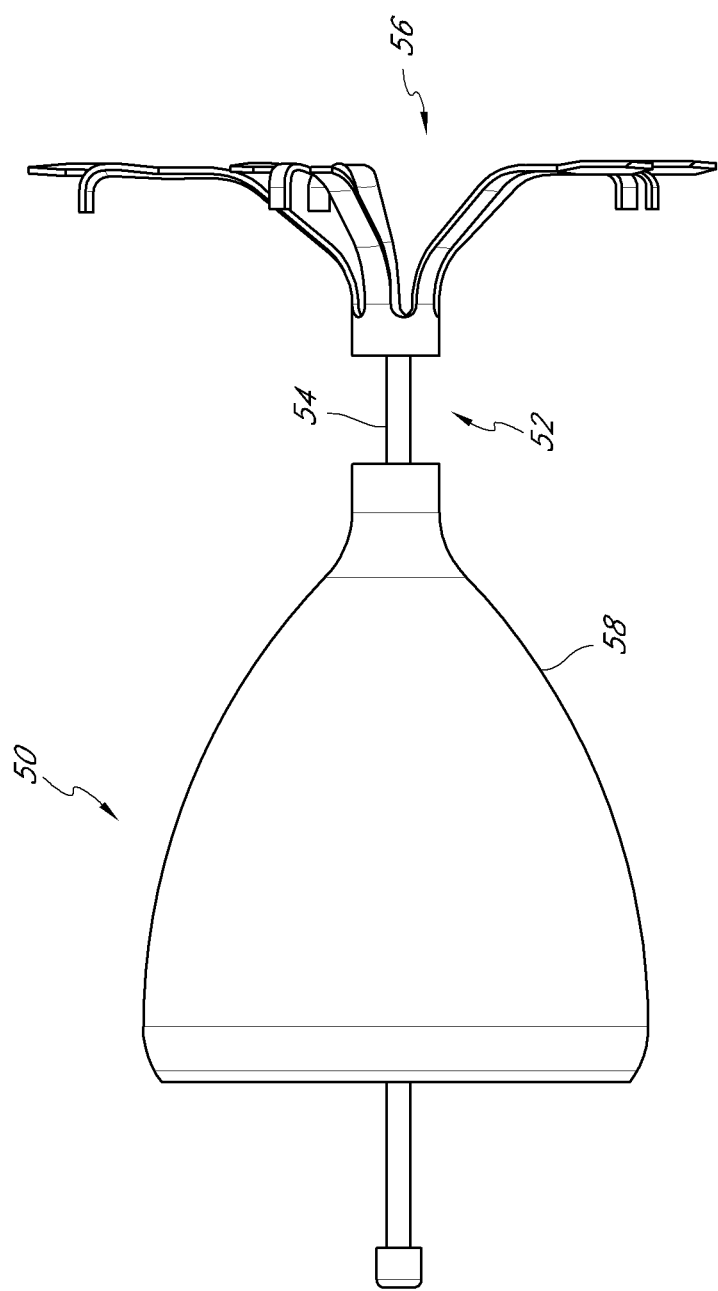
FIG. 2 is a side view of an implantable device with an articulable anchor.

FIG. 2 is a side view of an embodiment of an implantable device 50. The obstruction member 58 is coupled with the anchor 56 by a connecting mechanism 52. In the illustrated embodiment, the connecting mechanism 52 comprises a connecting member 54. The connecting mechanism 52 permits articulation between the obstruction member 58 and the anchor 56. In the illustrated position, the obstruction member 58 and the anchor 56 are collinear along the longitudinal axis of the implantable device 50. Through articulation of the connecting mechanism 52, the obstruction member 58 and the anchor 56 can be configured to no longer be collinear along the longitudinal axis of the implantable device 50. As one non-limiting example, the obstruction member 58 can be maintained at an unaltered orientation while the connecting mechanism 52, either by pivoting or flexing, can continue to couple the obstruction member 58 to the anchor 56 while the anchor 56 is moved to a different orientation than that of the obstruction member 58. In some embodiments, the connecting mechanism 52 can permit axial movement, changing the distance between the distal end of the obstruction member 58 and the proximal end of the anchor 56. In some embodiments, the articulation of the connecting mechanism 52 is accomplished through discrete pivotal orientation changes. In other embodiments, the connecting mechanism 52 is configured to articulate through continuous flexing, such as the bending of a flexible member. In still other embodiments, the connecting mechanism 52 can be configured to permit changes in orientation between the obstruction member 58 and the anchor 56 by limiting separation between the obstruction member 58 and the anchor 56 when the connecting mechanism 52 is not rigidly coupled to the two components. In these embodiments, the connecting mechanism 52 can comprise a tether or other limiting component.

Figure 3:
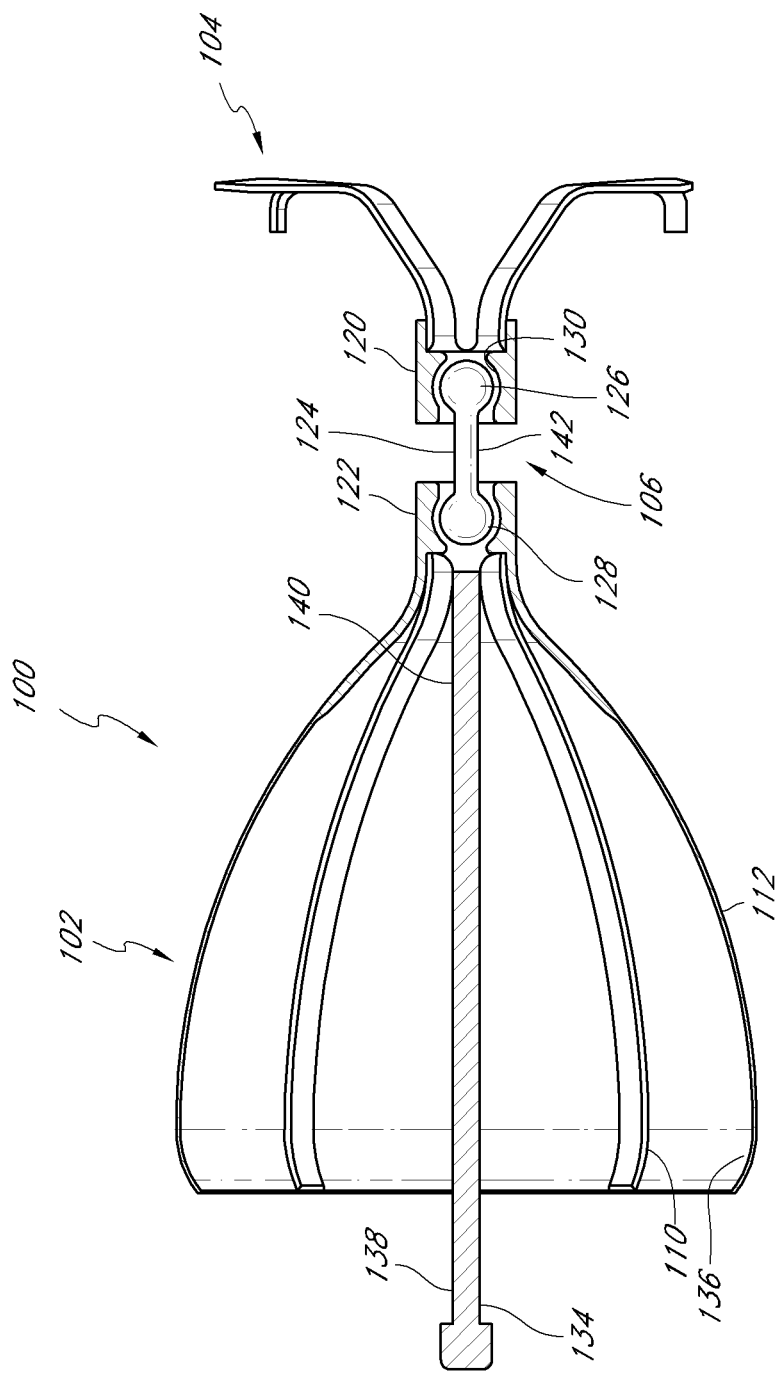
FIG. 3 is a cross-sectional view of the device of FIG. 2.

FIG. 3 is a cross-sectional view of another embodiment of an implantable device 100. The implantable device 100 is configured to permit an angled position. The implantable device 100 can be positioned in a naturally angled air passageway (e.g., a bifurcated air passageway, tortuous air passageway, etc.) in a lung. The implantable device 100 has an anchor sufficiently articulable so as to permit deployment of the implantable device 100 within the angled air passageway without substantially altering the natural geometry of the air passageway. The implantable device 100 can effectively function even though the obstructing member 102 conforms to the natural shape of the air passageway. The implantable device 100 can be generally similar to the implantable device 10 of FIG. 1, and accordingly, the following description of the implantable device 100 can equally apply to the implantable devices described below, unless indicated otherwise.

As used herein, the term "implantable device" is a broad term and is used in its ordinary meaning and includes, without limitation, articulated implantable devices, actuatable implantable devices, and other implantable devices that have one or more means for providing articulation, actuating, or flexibility between an anchor and a functional member, such as an obstruction member. The implantable devices may have any number of pivot points or flexible portions. These implantable devices can be placed along tortuous pathways, such as a section of a lung passageway that is substantially curved along its length. Some embodiments include a means for providing flexibility that comprises any combination of a biasing member, a flexible member, a ball and socket arrangement, a joint, a linkage, a hinge, and/or a flexible connector. As such, the flexible implantable device can be selectively curved or angled along its length to match the shape of the air passageway.

The illustrated implantable device 100 comprises an obstructing member 102 articulably and pivotally connected to an anchor system 104. The anchor system 104 can be moved relative to the obstructing member 102 to a desired position depending on the functional application of the device 100. An articulating connecting portion 106 connects and permits movement between the obstructing member 102 and the anchor system 104. The articulating connecting portion 106 permits articulation of the device 100 such that the device 100 can be implanted in curved air passageways without significantly altering the natural geometry of the air passageway. For example, the implantable device 100 can span a bronchial branching section of a lung. The implantable device 100 can be articulated repeatedly (e.g., during normal lung functioning) without appreciable trauma to the lung, or to the implantable device 100. Traditional stent-based devices for implantation in air passageways are typically rigid elongated structures that are not suitable for placement in bifurcated or substantially curved air passageways. These stent-based devices maintain their linear configuration thus rendering them unsuitable for use in these types of air passageways.

With reference again to FIG. 3, the articulating connecting portion 106 can have various configurations for permitting relative movement between the anchor system 104 and the obstructing member 102. In some embodiments, including the illustrated embodiment, the articulating connecting portion 106 comprises at least one ball and socket arrangement. The illustrated anchor system 104 has an anchor socket 120 comprising a generally spherical cavity that holds one end of the connecting rod 124, while the obstructing member 102 has an obstructing socket 122 that holds the other end of the connecting rod 124.

The connecting rod 124 has a first end 128 and an opposing second end 126. Each of the ends 126, 128 is generally spheroidal and sized to be received by the corresponding socket 122, 120. The spheroidal shape the ends 126, 128 can be integral with the connecting rod 124 or generally spheroidal-shaped members can be coupled to or mounted on the ends 126, 128. The first end 128 is rotatably mounted in the obstructing socket 122. The second end 126 is rotatably mounted in the anchor socket 120. As such, the sockets 120, 122 can rotate freely about the ends of the connecting rod 124. Thus, the implantable device 100 has a plurality of joints that permit articulation. The implantable device can have any number of articulable connecting portions for a particular application.

To reduce wear of the balls and the sockets, the surface(s) of the sockets and/or ends 126, 128 can be coated with a material to reduce frictional interaction. For example, the interior surface 130 of the anchor socket 120 can comprise one or more of the following: a somewhat lubricious material (e.g., Teflon®), ceramics, metals, polymers (preferably hard polymers), or combinations thereof. However, other materials can be utilized to limit or inhibit wear between the connecting rod 124 and the obstructing member 102 and/or the anchor system 104. When the implantable device 100 is deployed in the lungs, the anchor socket 120 can move, preferably slightly, with respect to the ball at the second end 126 during normal respiration. The wear-resistant surfaces can minimize debris build up that can impede performance of the implantable device 100. In view of the present disclosure, one of ordinary skill in the art can determine the appropriate combination of materials, geometry of the ball and socket arrangement, and the length of the connecting rod 124 to achieve the desired positioning of the implantable device 100.

The connecting rod 124 can have a one-piece or multi-piece construction. In some embodiments, the connecting rod body 142 and the ends 126, 128 are formed of a single material (e.g., a metal such as Nitinol or titanium). In other embodiments, the connecting rod body 142 is formed of a flexible material, and the ends 126, 128 are formed of a somewhat hard, rigid material, such as a ceramic.

The connecting rod 124 can be generally straight, as shown in FIG. 3. However, the connecting rod 124 can have other configurations based on clinical need. For example, the connecting rod 124 of FIG. 8 has an angled shape that allows placement of the implantable device in a complex shaped airway (e.g., an airway with sharp curves, branching portions, etc.).

With continued reference to FIG. 3, an elongated member 134 includes a rod 138 having an end portion 140 that is connected to the obstructing member frame 136. The end portion 140 can be connected to the frame 136 by one or more mechanical fasteners, adhesives, welding, boarding, interference fit, threads, or other suitable coupling means for securely coupling the rod 138 to the frame 136. In some embodiments, including the illustrated embodiment, the rod 138 is connected to the interior portions of the struts 110, although the rod can be connected to other portions of the frame 136. The rod 138 can also be formed integrally with at least a part of the frame.

Figure 4:
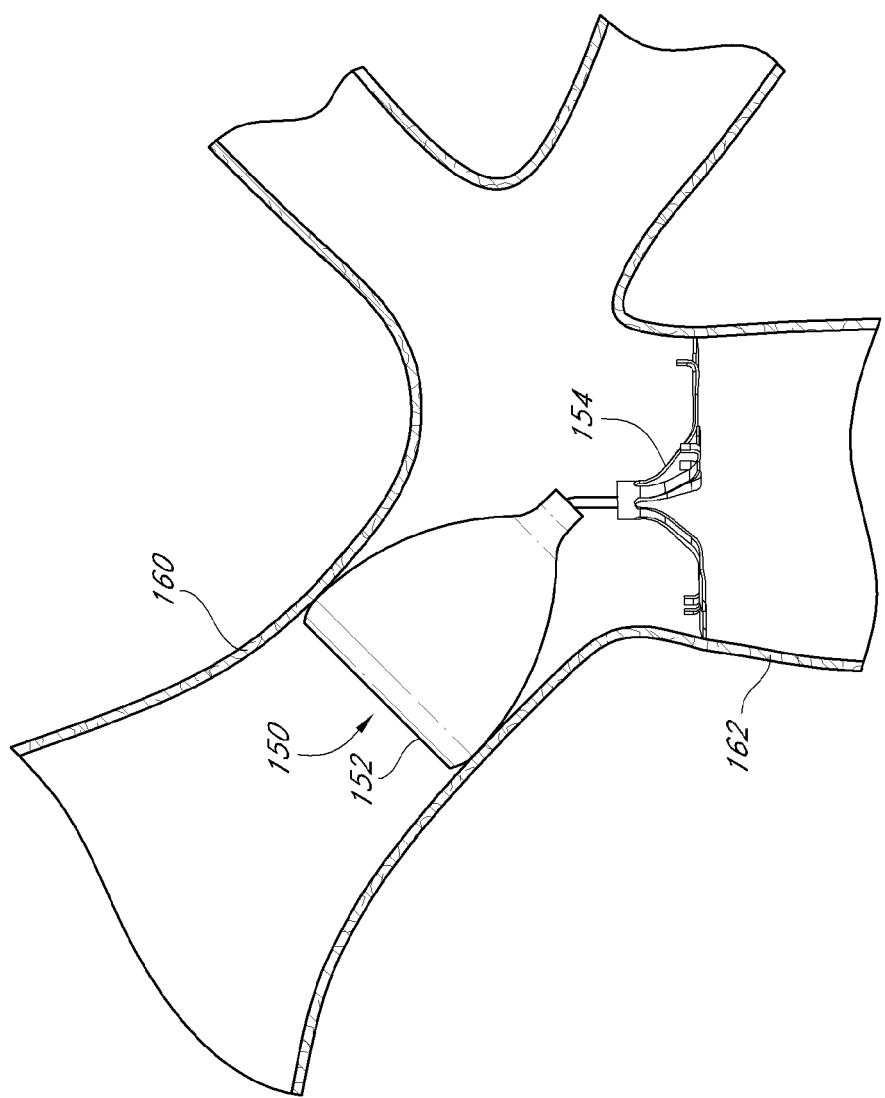
FIG. 4 is a cross-sectional view of an air passageway and an implantable device with an articulable anchor that spans a bifurcated air passageway.

As shown in FIG. 4, the implantable device 150 can be placed at a branching air passageway of the bronchial tree. The obstructing member 152 is within a proximal passageway 160 and the anchor system 154 is positioned within a distal sub-branch air passageway 162. The implantable device 150 can therefore span the junction 164 of the air passageway of the lung and, thus, permits flexibility in positioning of the device 150. The air passageway can generally retain its natural shape, such as its shape before implantation of the implantable device 150, to minimize trauma to the lung tissue. The orientations of the implantable devices are not limited solely to the illustrated orientations. The implantable device 150 can be reversed from the illustrated orientation so that the anchors are located proximally of the obstruction member. Thus, the implantable device 150 can be oriented to permit air flow in any desired direction.

The implantable device 150 can also be implanted in non-branching portions of lungs. If desired, the implantable device 150 can be implanted in continuous air passageways that are generally straight, curved, angled, or having any other configuration. Because the implantable device 150 can assume various configurations, there is significant flexibility in selecting a deployment site. The implantable device 150 can also be implanted in air passageways that have a substantially constant or varying cross-section. Advantageously, the physician can implant the implantable device 150 at various locations throughout the lung to treat specific portions of the lung. If the implantable devices are in the form of occluding devices or flow regulating devices (e.g., a one-way valve, flow resistor, etc.), these devices can be implanted proximally of, and adjacent to, the diseased portions of a lung, thus maximizing the amount of healthy lung tissue that can function, even if the diseased lung tissue is in the far distal portions of the bronchial tree.

Figure 5:
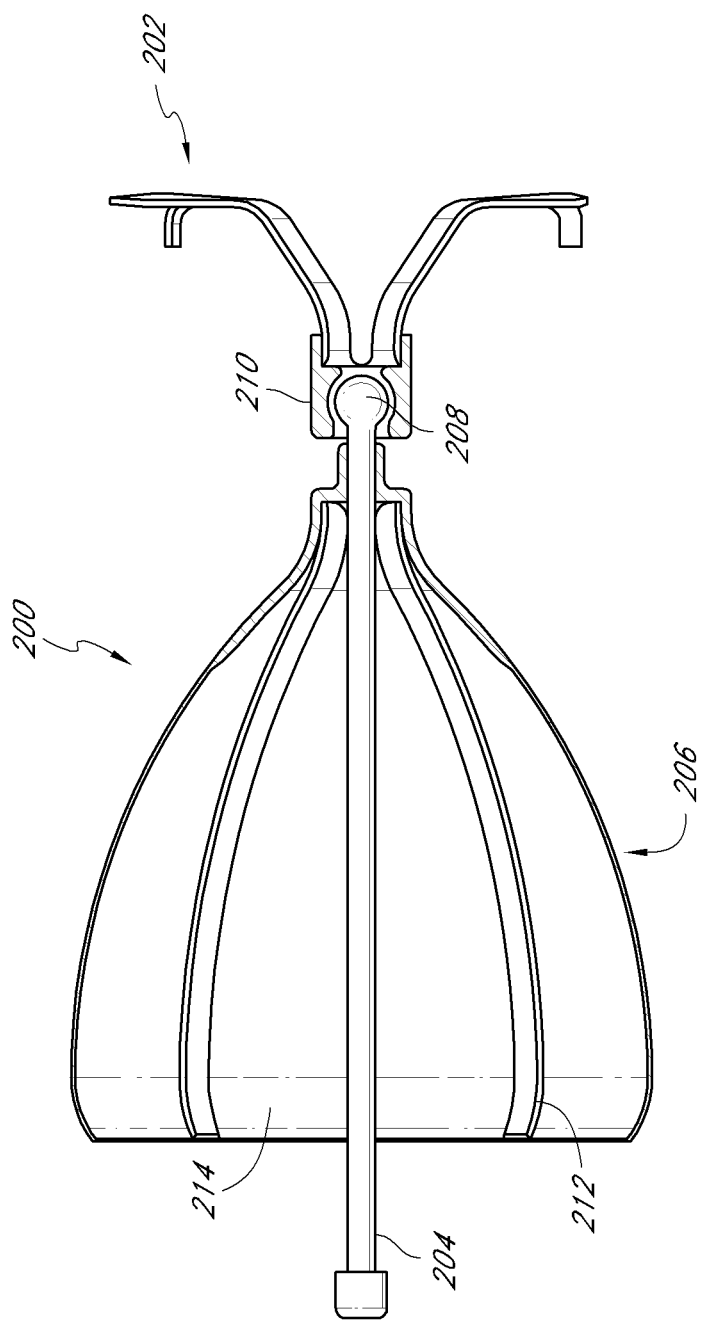
FIG. 5 is a cross-sectional view of an implantable device with an articulable anchor in accordance with another embodiment.

FIG. 5 illustrates an implantable device 200 that comprises an anchor system 202 that is pivotally coupled to an elongated member 204 that extends through the obstructing member 206. The elongated member 204 has a generally spheroidal member 208 that is rotatably mounted in an anchor socket 210 of the anchor system 202. The obstructing member 206 can be fixedly attached at some point along the elongated member 204.

To secure the obstructing member 206 to the elongated member 204, a portion of an obstructing member frame 212 and/or a membrane 214 can be coupled to the elongated member 204. In the illustrated embodiment, the struts of the obstructing member frame 212 and the membrane 214 are both coupled to the outer surface of the elongated member 204.

Once deployed, the implantable device 200 illustrated in FIG. 5 can be retained in place by the anchor system 202. The implantable device 200 can be positioned in a non-linear lumen, such as those illustrated in FIG. 4, because the anchor system 202 may remain at a first orientation while the obstructing member 206 is pivoted to a second orientation by the generally spheroidal member 208 and the anchor socket 210. The obstructing member 206 can be configured to move axially from the anchor system 202 through travel along the elongated member 204, which can be limited to prevent inefficient operation of the implantable device 200.

Figure 6:
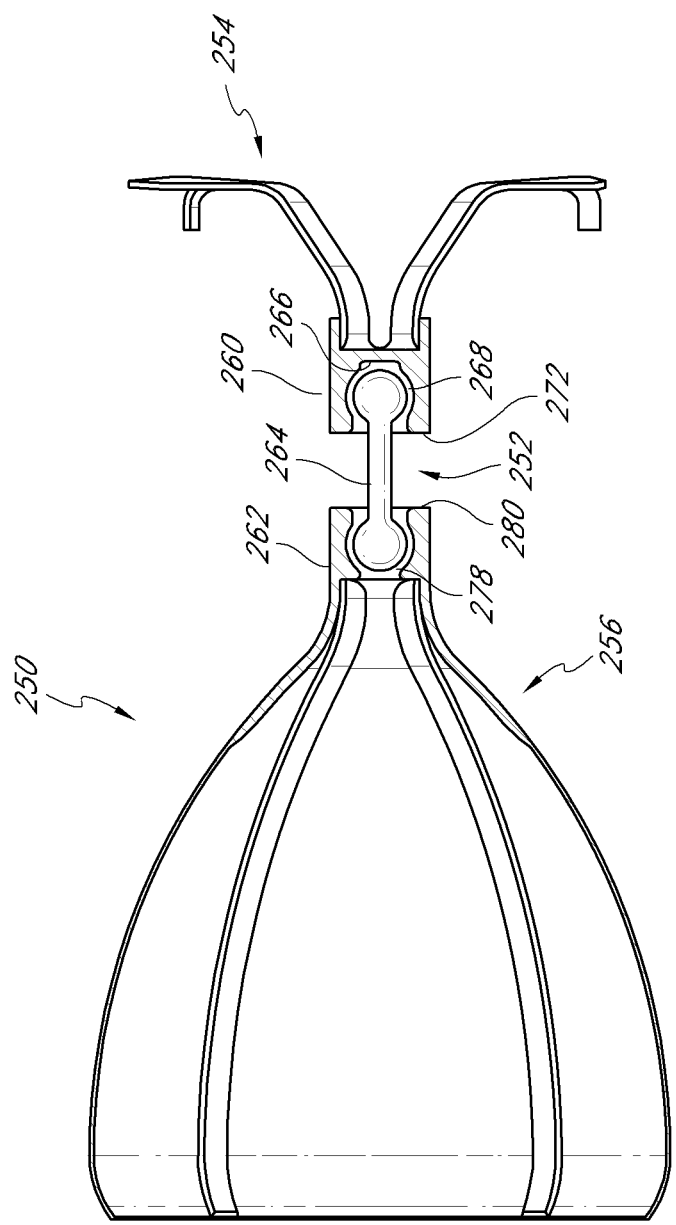
FIG. 6 is a cross-sectional view of an implantable device with an articulable anchor in accordance with another embodiment.

FIG. 6 is a cross-sectional view of a implantable device 250 that has an articulable connecting portion 252 that permits axial movement between an anchor system 254 and an obstructing member 256. The connecting portion 252 includes a holder 260 of the anchor system 254 and a holder 262 of the obstruction member 256. Each of the holders 260, 262 is configured to receive an end of a connector 264. The illustrated connector 264 has enlarged ends that are held by the holders 260, 262. The chambers 268, 278 of the holders 260, 262, respectively, permit axial movement of the connector 264. The enlarged ends of the connector 264 that are held by the holders 260, 262 can also be constructed to permit pivotal movement in addition to axial movement.

The anchor system 254 and the obstructing member 256 of the device 250 can move freely towards and away from each other. However, one or more biasing members (not shown) can be positioned between the anchor system and obstructing member of the implantable device to adjust positioning of the implantable device. The biasing member can cooperate with the connecting portion to ensure that the implantable device remains in a desired position.

Figure 7:
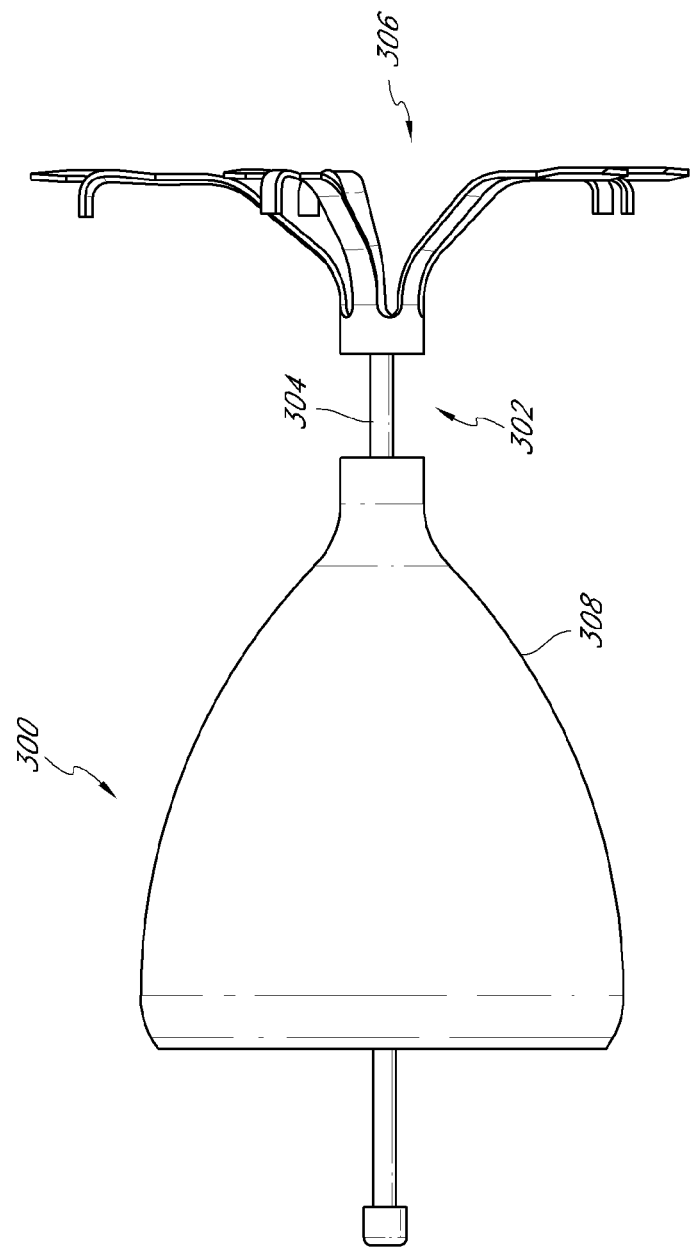
FIG. 7 is a side view of an implantable device with an articulable anchor in accordance with another embodiment.

FIG. 7 illustrates an implantable device 300 that has an articulating connecting portion 302 that includes a flexible member 304 connected to the anchor system 306 and the obstructing member 308. The flexible member 304 can comprise a somewhat flexible elongated member (e.g., a solid rod, a hollow tube, ribbon, etc.) and can comprise metal, polymers (preferably a somewhat rigid polymer), filaments, and the like. The flexible member 304 preferably does not substantially stretch or buckle when an axial force is applied thereto. Alternatively, the flexible member 304 can be configured to allow significant axial movement between the anchor system 306 and the obstructing member 308. The flexible member 304 can be, for example, a tether that holds together and limits the axial movement of the anchor system 306 away from the obstructing member 308. However, the flexible member 304 may be easily collapsed as the anchor system 306 is moved towards the obstructing member 308. The flexible member 304 can comprise a rope, wire, filaments, or other suitable member for providing relative movement between the anchor system 306 and the obstructing member 308.

Figure 8:
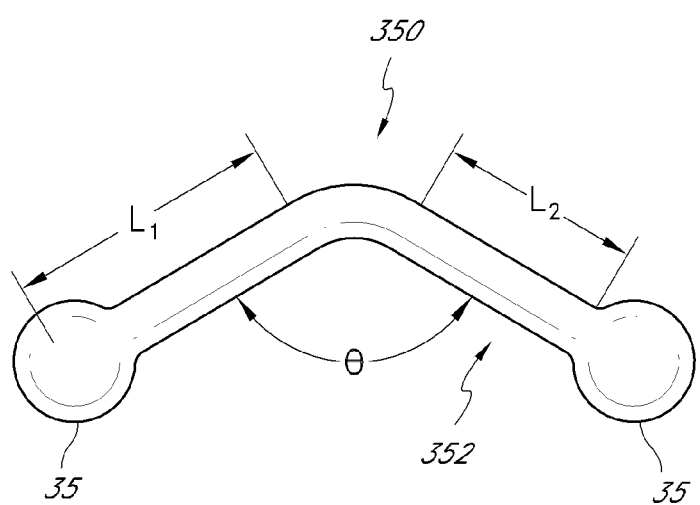
FIG. 8 is a side view of a flexible connector for use in an implantable device with an articulable anchor.

With reference to FIG. 8, the connecting rod 350 can have or bend to have an angled central portion 352 that defines an angle θ. The length L1 and L2 can be selected to achieve the desired orientation and size of an implantable device. If the implantable device is deployed at a sharp bend of an air passageway, the angle θ can be matched with the angle of the bend to generally align the longitudinal axis of an anchor system with one of the passages and the longitudinal axis of an obstructing member with the other passage. The implantable device, for example, can include a connecting rod for deployment in air passageways that together form an acute angle. Accordingly, the configuration of the connecting rod 350 can be selected based on the target deployment site.

Figure 9:
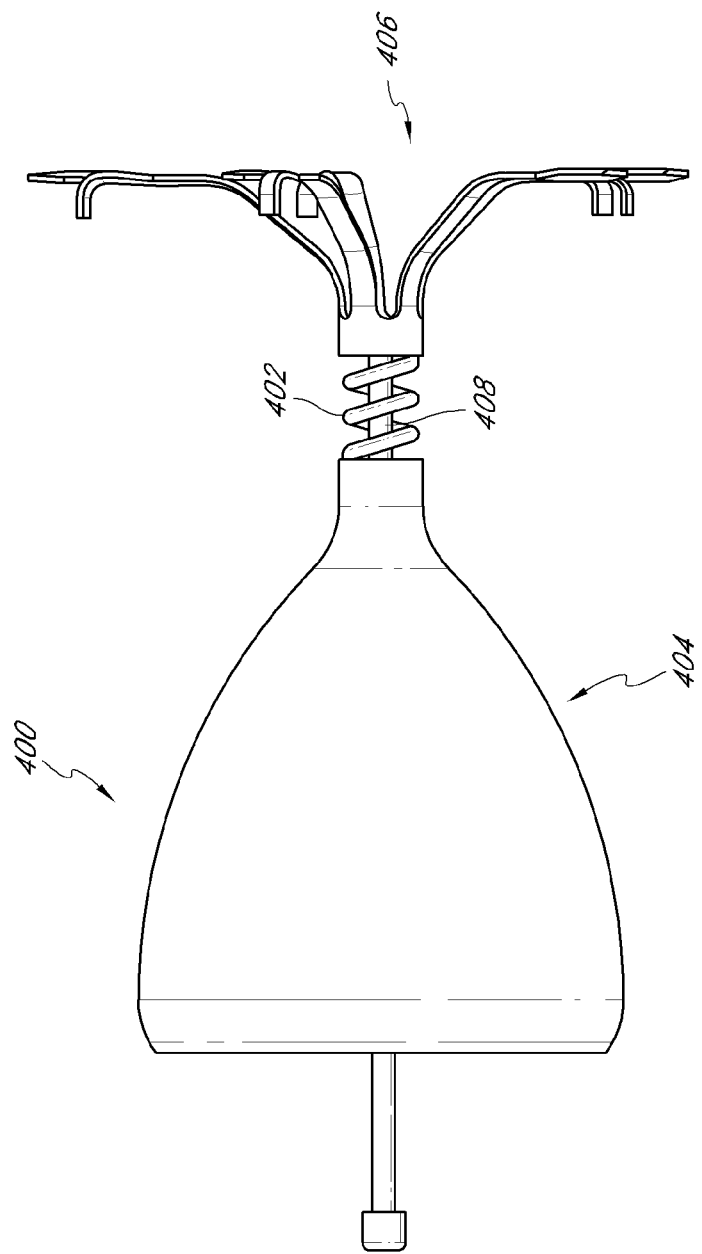
FIG. 9 is a side view of an implantable device with an articulable anchor having a biasing member and a connector positioned between an obstruction member and the anchor system.

As illustrated in FIG. 9, the implantable device 400 can have a biasing member 402 positioned between an obstructing member 404 and an anchor system 406. One example of such a biasing member is a helical spring. In the illustrated embodiment, a tether 408 extends through the biasing member 402 between the obstructing member 404 and the anchor system 406. Other embodiments can have a tether 408 connecting the obstructing member 404 and an anchor system 406 that does not extend through the biasing member 402 and instead passes at least partially outside the biasing member 402. Alternatively, a flexible cylindrical member (not shown) can extend between the obstructing member 404 and the anchor system 406, substantially completely enclosing the biasing member 402. The tether can also be a connector such as the one illustrated in FIG. 7.

Figure 10A:
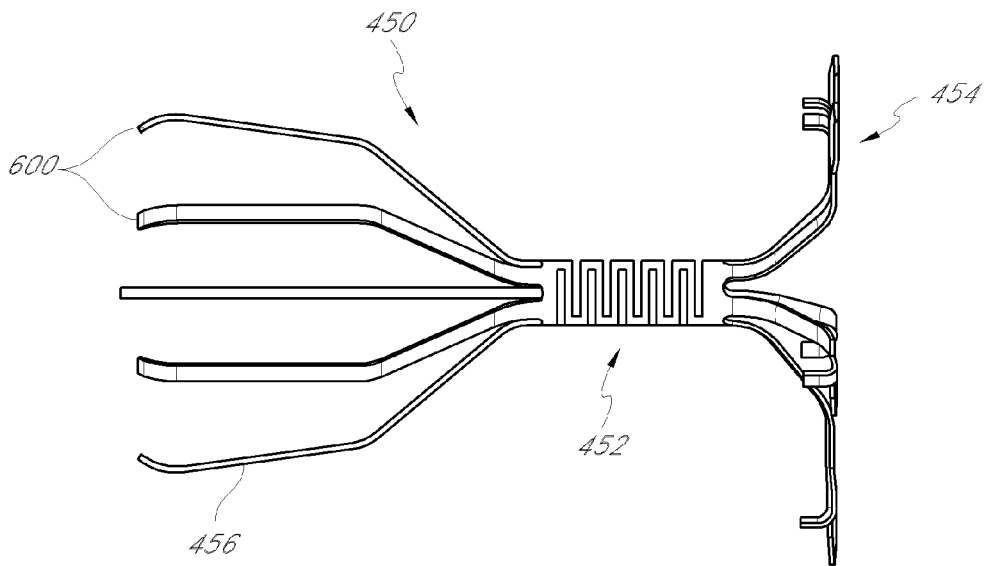
FIGS. 10A-10C are side views of alternative embodiments of frames for implantable devices with articulable members embodied as flexible connectors.
Figure 10B:
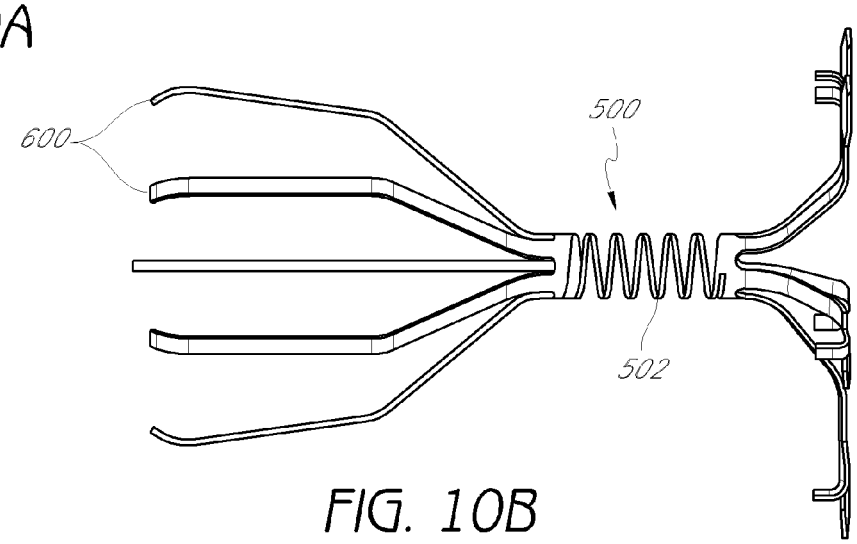
Figure 10C:
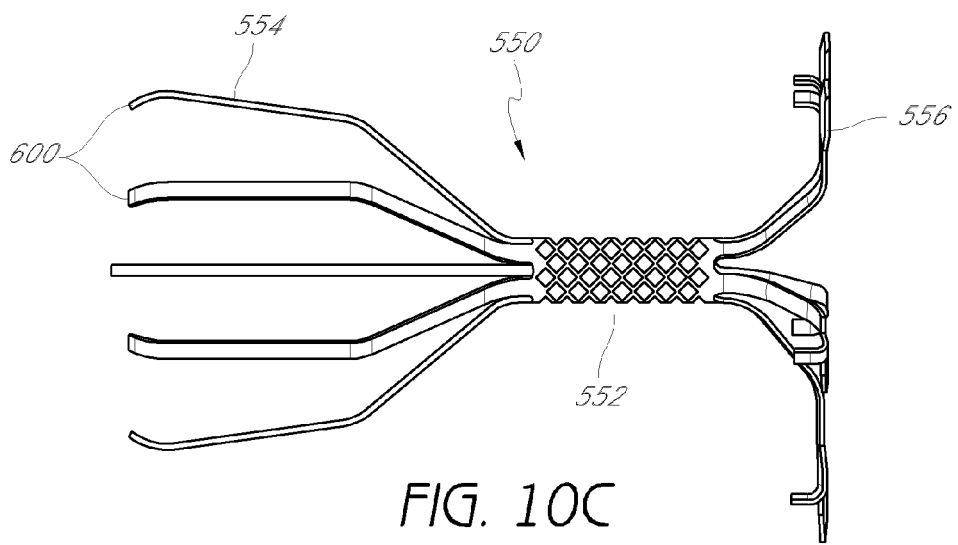

FIGS. 10A-10C illustrate various embodiments of support frames of implantable devices, each having a means for flexing. Each of the support frames has a flexible connecting portion that permits relative movement between an anchor system and an obstructing member frame. The frames as illustrated do not have membranes; however, any of various types of membranes can be applied to the obstructing member frames. FIG. 10A illustrates a frame support 450A that includes a flexible connecting portion 452A in the form of slots in an alternating pattern. The connecting portion 452A can be an integral piece with the frame, as illustrated, or can be coupled or mounted to an anchor system 454A and an obstruction frame 456A. The flexible connecting portion 452A can be formed by cutting slots out of a tube. The number and size of the slots can be selected to achieve the desired flexibility. Additionally, the material used to construct the connecting portion can be selected for its flexibility characteristics.

FIG. 10B illustrates a frame support 500B that is generally similar to the frame support 450A of FIG. 10A. In the illustrated embodiment, the frame support 500B includes a flexible connecting portion 502B in the form of a spring member extending axially along the longitudinal axis of the frame support 500B. As such, the spring member can be arranged in a spiral fashion about the longitudinal axis of the flexible connecting portion 502B. The illustrated spring member is in the form of a helical spring, although other types of springs or resilient members can be utilized. The spring can comprise the connecting member alone or can act as a biasing member, as described above. Additionally, as described above, the spring can be faulted integrally with the frame, or serve as a coupler for both an anchor system and obstruction frame.

FIG. 10C illustrates a frame support 550C that comprises a flexible connecting portion 552C comprising a mesh. The connecting portion 552C can comprise a mesh of various sizes, with large or small mesh spaces. Additionally, the mesh can be constructed of a variety of materials, such as metals, synthetics, or any other resilient material. The mesh can permit flexing, as when the obstructing frame 554C and anchor system 556C are positioned at different orientations, as described above. In some embodiments, the mesh can also permit axial compression along the longitudinal axis of the frame support 550C. As described, the mesh can be formed integrally with the frame, or be mounted or coupled at either end to the obstructing frame 554C and anchor system 556C.

The illustrated struts 600A, 600B, 600C of FIGS. 10A-10C each have two generally elongated straight portions connected by a bend. The struts 600A, 600B, 600C can also have a continuously curved configuration similar to the struts described above. The frame supports can carry a membrane to form an obstructing member, such as an obstructing member adapted to function as a valve (preferably a one-way valve). The connecting portions can enhance the seating of the obstructing member within an air passageway to enhance valve functioning.

Figure 11:
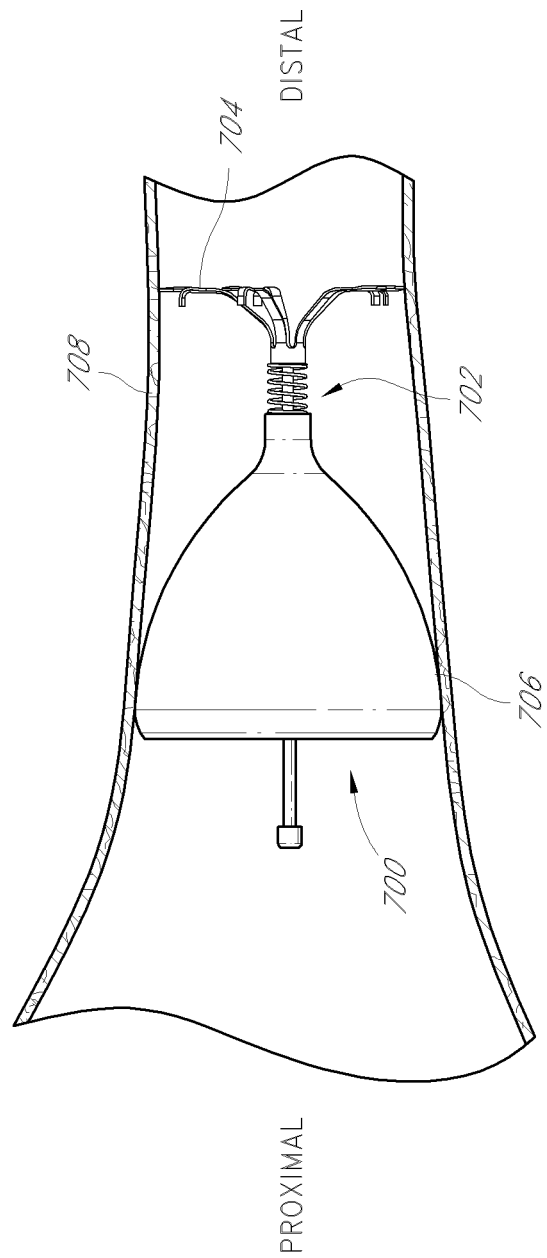
FIG. 11 is a cross-sectional view of an air passageway and a flexible implantable device positioned in the air passageway

With reference to FIG. 11, an implantable device 700 is illustrated as having a flexible connecting portion 702, such as the one shown in FIG. 10A. The implantable device 700 is deployed and implanted in an air passageway 708 and is held in place by its anchor system 704. The flexible connecting position 702 can apply a force to the obstructing member 706 of the implantable device 700 to enhance seating between the membrane of the obstructing member 706 and the wall 708. Thus, a bias of the flexible connecting portion 702 can ensure that an effective seal is maintained between the obstructing member 706 and the wall 708, thereby limiting or preventing the flow of air distally past the implantable device 700. Advantageously, the implantable device 700 can permit the passage of air proximally past the obstructing member 706 when the pressure differential across the implantable device 700 is sufficiently high. As the air flows proximally past the obstructing member 706, the flexible connecting portion 702 can apply a distally directed force. When the pressure differential is reduced a sufficient amount, the obstructing member 706 is pulled distally against the air passageway wall 708 to once again faun a seal with the air passageway wall. Thus, the obstructing member 706 can move slightly during normal lung functioning while the anchor system 704 can remain securely fixed in place. The flexible connecting portion 702 can therefore enhance the valving action of the implantable device 700.

If desired, the connecting portion 702 can also be used to position the anchors 704 and the obstructing member 706 along a tortuous path within a lung, as shown in FIG. 4 above. The connecting portion 702 can be positioned along sharp turns that may be unsuitable for rigid valves, such as stent-based devices.

All patents and publications mentioned herein are hereby incorporated by reference in their entireties. Except as further described herein, the embodiments, features, systems, devices, materials, methods and techniques described herein may, in some embodiments, be similar to any one or more of the embodiments, features, systems, devices, materials, methods and techniques described in U.S. patent application Ser. Nos. 10/409,785 (U.S. Publication 2004-0200484), filed Apr. 8, 2003; 09/951,105 (U.S. Publication No. 2003/0050648A1), filed Mar. 13, 2003; 10/848,571, filed May 17, 2004; 10/847,554, filed May 17, 2004; 10/418,929, filed Apr. 17, 2003; 10/081,712 (U.S. Publication 2002-0112729), filed Feb. 21, 2002; 10/178,073 (U.S. Publication 2003-0154988), filed Jun. 21, 2002; 10/317,667 (U.S. Publication 2003-0158515), filed Dec. 11, 2002; 10/103,487 (U.S. Publication 2003-0181922), filed Mar. 20, 2002; 10/124,790 (U.S. Publication 2003-0195385), filed Apr. 16, 2002; 10/143,353 (U.S. Publication 2003-0212412), filed Mar. 9, 2002; 10/150,547 (U.S. Publication 2003/0216769), filed May 17, 2002; 10/196,513 (U.S. Publication 2004-0010209), filed Jul. 15, 2002; 10/254,392 (U.S. Publication 2004/0059263), filed Sep. 24, 2002; 10/387,963 (U.S. Publication 2004-0210248), filed Mar. 12, 2003; 10/745,401, filed Dec. 22, 2003; U.S. Pat. Nos. 6,293,951; 6,258,100; 6,722,360; 6,592,594, which are hereby incorporated herein and made part of this specification. In addition, the embodiments, features, systems, devices, materials, methods and techniques described herein may, in certain embodiments, be applied to or used in connection with any one or more of the embodiments, features, systems, devices, materials, methods and techniques disclosed in the above-mentioned incorporated applications and patents.

The articles disclosed herein may be formed through any suitable means. The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments disclosed herein. Similarly, the various features and steps discussed above, as well as other known equivalents for each such feature or step, can be mixed and matched by one of ordinary skill in this art to perform methods in accordance with principles described herein. Additionally, the methods which are described and illustrated herein are not limited to the exact sequence of acts described, nor are they necessarily limited to the practice of all of the acts set forth. Other sequences of events or acts, or less than all of the events, or simultaneous occurrence of the events, may be utilized in practicing the embodiments of the invention.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein.

What is claimed is:

1. A method of inserting an occluding device into an air passageway of a lung comprising:
    accessing a non-linear air passageway with a catheter;
    inserting the occluding device into a lumen of the catheter, wherein the occluding device comprises a longitudinal axis and an articulable anchor for securing the occluding device within the non-linear air passageway in a manner that permits the articulable anchor to articulate substantially with respect to said occluding device such that the occluding device and the articulable anchor are non-collinear along the longitudinal axis of the occluding device; and
    deploying the occluding device within the non-linear air passageway.

2. The method of inserting an occluding device into an air passageway as in claim 1, wherein the articulable anchor comprises a plurality of resilient arms.

3. The method of inserting an occluding device into an air passageway as in claim 2, wherein the plurality of resilient arms comprises tapered distal ends to permit the resilient arms to penetrate walls of the air passageway.

4. The method of inserting an occluding device into an air passageway as in claim 1, wherein the occluding device comprises a plurality of struts having a first end that curves inward towards a longitudinal axis the occluding device and a second end that attaches to a junction of the second ends of the plurality of struts.

5. The method of inserting an occluding device into an air passageway as in claim 4, the occluding device further comprising a resilient membrane attached to the plurality of struts, wherein at least a portion of the resilient membrane wraps around the first end and curves inward towards the longitudinal access.

6. The method of inserting an occluding device into an air passageway as in claim 1, wherein the occluding device is a one-way valve.

7. The method of inserting an occluding device into an air passageway as in claim 6, wherein the one-way valve is configured to prevent inhalation air flow while allowing exhalation air flow.

8. The method of inserting an occluding device into an air passageway as in claim 1, further comprising engaging an elongate member to retract and re-deploy the occluding device within the non-linear passageway, wherein the elongate member is coupled to the occluding device.

9. The method of inserting an occluding device into an air passageway as in claim 1, wherein the occluding device comprises a substantially umbrella-shaped configuration.

10. The method of inserting an occluding device into an air passageway as in claim 1, wherein the deploying further comprises deploying the occluding device within the non-linear air passageway without substantially altering a natural geometry of the air passageway.

11. An implantable device for deployment in an air passageway, the device comprising:
    an occluding device comprising a first longitudinal axis, and
    an anchor for securing the occluding device within the air passageway, the anchor comprising a second longitudinal axis,
    wherein the occluding device comprises a plurality of struts having a first end that curves inward towards a longitudinal axis of the occluding device and a second end that attaches to a junction of the second ends of the plurality of struts, wherein the plurality of struts bias the occluding device against the wall of the air passageway, and wherein the anchor is an articulable anchor for securing the occluding device within the air passageway in a manner that permits the anchor to articulate substantially with respect to said occluding device, the occluding device and the anchor being coupled to allow the first axis and the second axis to be non-collinear.

12. The implantable device of claim 11, the occluding device further comprising a resilient membrane attached to the plurality of struts, wherein at least a portion of the resilient membrane wraps around the first end and curves inward towards the longitudinal access.

13. The implantable device of claim 11, wherein the articulable anchor comprises a plurality of resilient arms.

14. The implantable device of claim 13, wherein the plurality of resilient arms comprises tapered distal ends to permit the resilient arms to penetrate walls of the air passageway.

15. The implantable device of claim 11, wherein the air passageway is a non-linear air passageway.

16. The implantable device of claim 15, further comprising an elongate member coupled to the occluding device, wherein the elongate member is configured to be engaged by a catheter to retract and re-deploy the occluding device within the non-linear passageway.

17. The implantable device of claim 11, wherein the occluding device is a one-way valve.

18. The implantable device of claim 17, wherein the one-way valve is configured to prevent inhalation air flow while allowing exhalation air flow.

19. The implantable device of claim 11, wherein the occluding device comprises a substantially umbrella-shaped configuration.

20. The implantable device of claim 11, wherein the plurality of struts comprise one or more pairs of adjacent struts with a membrane extending therebetween to define a pathway.

* * * * *